United States Patent [19]
Lenke et al.

[11] Patent Number: 5,269,827
[45] Date of Patent: Dec. 14, 1993

[54] ANALYTICAL SAMPLE PREPARATION SYSTEM

[75] Inventors: James H. Lenke, St. Joseph; Peter M. Willis, Benton Harbor; Scott A. Ponegalek, Bridgman, all of Mich.

[73] Assignee: Leco Corporation, St. Joseph, Mich.

[21] Appl. No.: 664,052

[22] Filed: Mar. 1, 1991

[51] Int. Cl.⁵ ............................................. C03B 5/18
[52] U.S. Cl. ................................. 65/178; 366/211; 366/218; 432/156
[58] Field of Search ............... 65/178; 366/211, 217, 366/218; 432/156, 157

[56] References Cited

U.S. PATENT DOCUMENTS

| | | | |
|---|---|---|---|
| 2,804,777 | 9/1957 | Kerr-Lawson | 366/217 |
| 3,437,317 | 4/1969 | Micin | 366/211 |
| 3,451,794 | 6/1969 | Patterson | 65/178 |
| 3,890,089 | 6/1975 | Matocha | 432/11 |
| 4,045,202 | 8/1977 | Claisse | 65/178 |
| 4,329,136 | 5/1982 | Willay | 425/174.8 |
| 4,609,392 | 9/1986 | Claisse | 65/178 |

FOREIGN PATENT DOCUMENTS

| | | |
|---|---|---|
| 23693/88 | 2/1989 | Australia . |
| 2248479 | 5/1975 | France . |
| 1527321 | 10/1978 | United Kingdom . |

OTHER PUBLICATIONS

Corporation Scientifique Claisse Inc. Brochure, 10 pages.

Primary Examiner—Joye L. Woodard
Attorney, Agent, or Firm—Price, Heneveld, Cooper, DeWitt & Litton

[57] ABSTRACT

An instrument and system for the preparation of a sample for analysis provides a crucible holder which improves the holding and control of a melting crucible during operation of the device for agitating a powdered sample and flux while being heated. The crucible holder is coupled to an agitation assembly which provides independently controlled operation on two different axes using separately adjustable variable frequency and amplitude motion along each of the two operating axes to provide an finite number of agitation patterns for the crucible. In one preferred embodiment of the invention, the heating flame is controlled by controlling the supply of compressed air and a combustion gas. In another preferred embodiment of the invention, a pilot burner is provided which both ignites the main burner located under the crucible and preheats the casting dish to a temperature which is substantially the same as the crucible. The pilot also can control air only flow directed to the casting dish for controllably cooling the sample melt to form the sample bead.

15 Claims, 22 Drawing Sheets

ANALYTICAL SAMPLE PREPARATION SYSTEM

BACKGROUND OF THE INVENTION

The present invention pertains to an apparatus and a method for the preparation of a sample bead for use in X-ray fluorescence spectroscopy or other analytical methods such as atomic absorption or inductively coupled plasma.

BACKGROUND OF THE INVENTION

Several machines are commercially available which provide the mixing and heated fusion of a powdered sample together with a flux to provide a solid glass-like sample bead or button for analysis by X-ray fluorescence spectroscopy or other analytical methods. Samples to be analyzed include materials such as silicon dioxide, cement, aluminum dioxide, calcium dioxide, magnesium oxide and slag, which are analyzed for the content of their active elements, typically using X-ray fluorescence spectroscopic analysis. To provide a sample in a form which can be used in connection with such an analyzer, it must be formed into a solid smooth-surfaced shape.

Existent machines for providing such a sample incorporate a crucible holding mechanism, which, while the crucible is being heated with the sample and flux combined to fuse the material, is rotated using a generally circular motion. One device also provides, tilting of the crucible while it is rotated to provide a continuous oscillatory mixing of the flux and sample as it is heated to a melting temperature. Such prior art mixing devices rely upon specially shaped crucibles to assist in the mixing action. This increases the cost of the already expensive platinum crucibles and interferes with the use of such a specialized crucible for other purposes. With such prior art devices, agitation, although in a multiple plane pattern, is not controllable as to frequency amplitude or flexibility as to path of travel of the crucible. With different specimens, different viscosities of the sample melt are encountered. It has been discovered that in order to provide a homogeneous mix with prior art devices, an excessive length of time is necessary to achieve the necessary mixing action of the sample and flux if achievable at all.

In the prior art systems, typically only low and high level melting temperatures are available utilizing a mixture of oxygen and propane in systems which do not provide temperature control flexibility for different types of samples to achieve sample preparation. With lack of temperature control of the flame used for the sample melt, it is possible that excessive temperatures can result in the generation of undesirable by-products such as silicon tetrafluoride ($SiF_4$) which is a gas which escapes the crucible and therefore changes the concentration of the samples to be tested. Further, with the use of pure oxygen and propane excessive temperatures can be reached which actually can melt the platinum crucible.

Also, in the prior art systems, the devices poured the mixed molten sample or melt into a casting dish for subsequent cooling into the desired sample shape. However, the dishes typically are positioned above the melting crucible and therefore the temperature of the dishes does not correspond closely to that of the crucible and during the pouring step, a sample can cool in an uneven manner thereby crystallizing improperly and possibly cracking rendering the sample unusable.

Further, sample preparation apparatus of this general type in the past have used either somewhat massive crucible holders which thermally interfere with the even heating of the crucible or relatively light-weight spring clips which although not thermally interfering with the crucible tend to lose their tension over a period of use, particularly when subjected to such high temperatures and which also can damage the platinum crucibles when forced into and out of the holding clips. Further, the clips are somewhat difficult to work with using normal laboratory tongs for handling the crucibles.

Finally, in the existent machines used for preparation of X-ray fluorescence samples, it is desired to controllably cool the sample melt once poured into the casting dish. This has been accomplished in the past by utilizing a separate fan or air control and delivery system which directs air over the casting dish for cooling. Although providing adequate cooling, it does not do so in a controlled manner and requires additional structure to achieve.

SUMMARY OF THE PRESENT INVENTION

The system of the present invention provides an entirely new apparatus for the preparation of a sample for analysis by providing according to one aspect of the invention, a unique crucible holder which improves the holding and control of the melting crucible during operation of the device for agitating a powdered sample and flux while being heated. The crucible holder is coupled to an agitation assembly which provides independently controlled operation on two different axes using separately adjustable variable frequency and amplitude motion along each of the two operating axes to provide a finite number of agitation patterns for the crucible. In one preferred embodiment of the invention, the heating flame is controlled by the control of the supply of compressed air and a combustion gas such as propane to achieve a desired selectable temperature throughout the melting, agitation, and casting stages. In another preferred embodiment of the invention, a pilot burner construction is provided which provides for both igniting the main controlled burner located under the crucible and for separately heating the casting dish (or dishes in a multiple burner system) to a temperature which is substantially the same as the crucible such that during pouring of the sample melt from the crucible to the melting dish, the melt is not exposed to thermal shock. The system of the present invention provides a control for controlling air flow through the pilot assembly directed to the casting dish for controllably cooling the melt to form the sample bead or button. The system of the present invention also provides for the automatic introduction of a nonwetting agent prior to the pouring of the melt into a casting dish.

Systems embodying the present invention therefore provide an improved and more efficient sample preparation method and apparatus in which higher quality samples can be prepared during a reduced time period. The system also can be used for peroxide samples such as sodium-peroxide ($Na_2O_2$) and other samples in which casting dishes are unnecessary and controlled oooling of the crucible is achieved directly through the burner.

These and other features, objects and advantages of the present invention, will become apparent upon reading the following description thereof together with reference to the accompanying drawings in which:

DETAILED DESCRIPTION OF THE PREFERRED EMBODIMENTS

Figure 1:
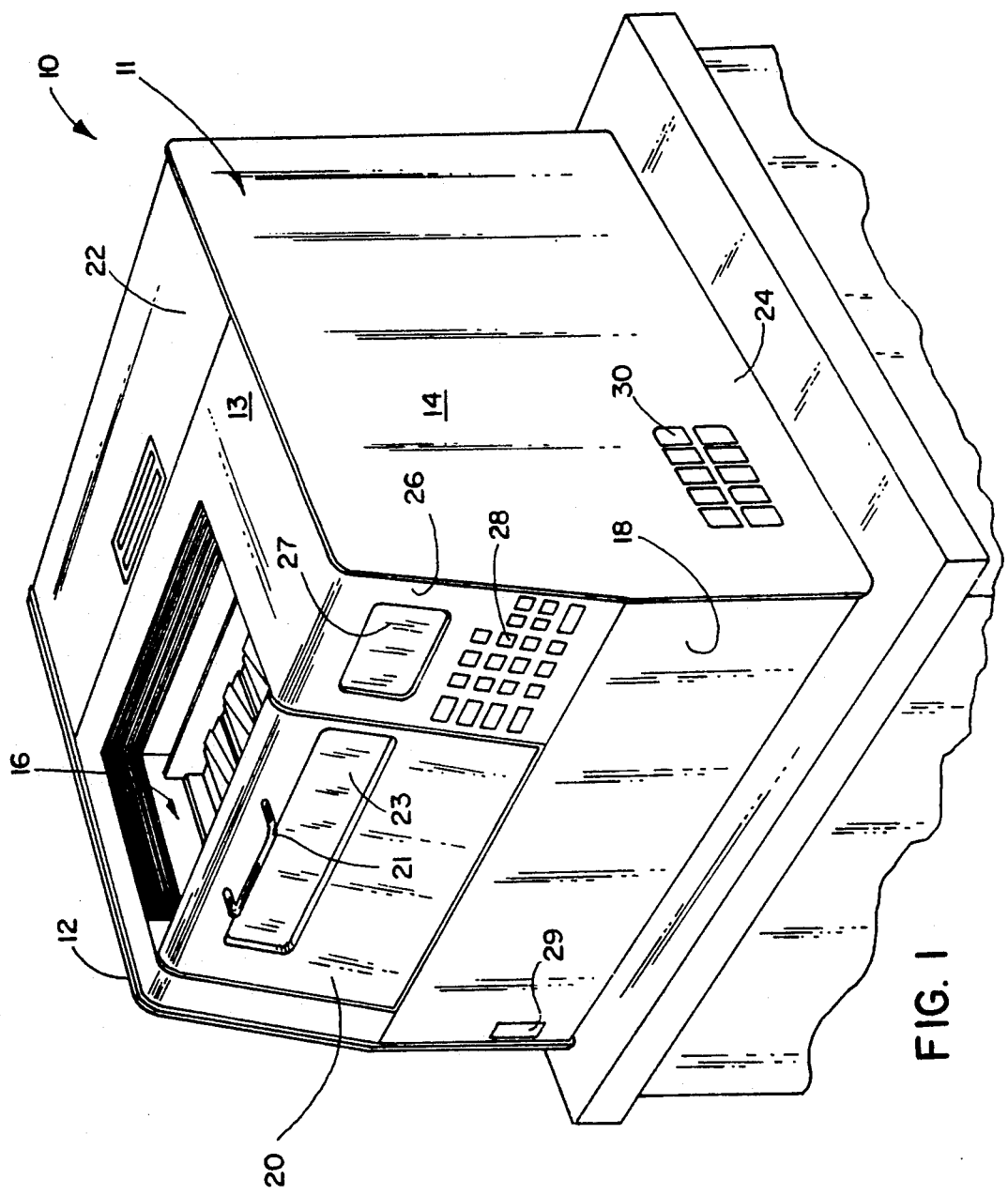
FIG. 1 is a perspective view of a sample preparation instrument embodying the present invention.

Referring initially to FIG. 1, there is shown an instrument 10 embodying the various aspects of the present invention. Instrument 10 includes a cabinet 11 having sidewalls 12 and 14, an open top 16, and a front panel 18 with a door 20 opening for access to the sample preparing apparatus contained within instrument 10. The rear portion of the top of the machine includes a cover panel 22 which can be opened for access while the cabinet rests on a support base 24. Mounted to an upper front panel 26 of instrument 10 is a keyboard 28 including a numeric keypad and other pushbutton control switches for controlling the instrument in connection with the electrical control circuit shown in FIG. 19. Door 20 includes a handle 21 for operation of the pivot down door and a viewing window 23 so that the instrument operation can be viewed safely from the front of the instrument. Similarly, front panel 26 includes a viewing window 27 for a similar purpose. The instrument 10 includes a master on-off switch 29 and suitable venting apertures such as vent 30 in sidewall 14. The rear of the cabinet also includes an access door and suitable venting apertures.

Figure 2:
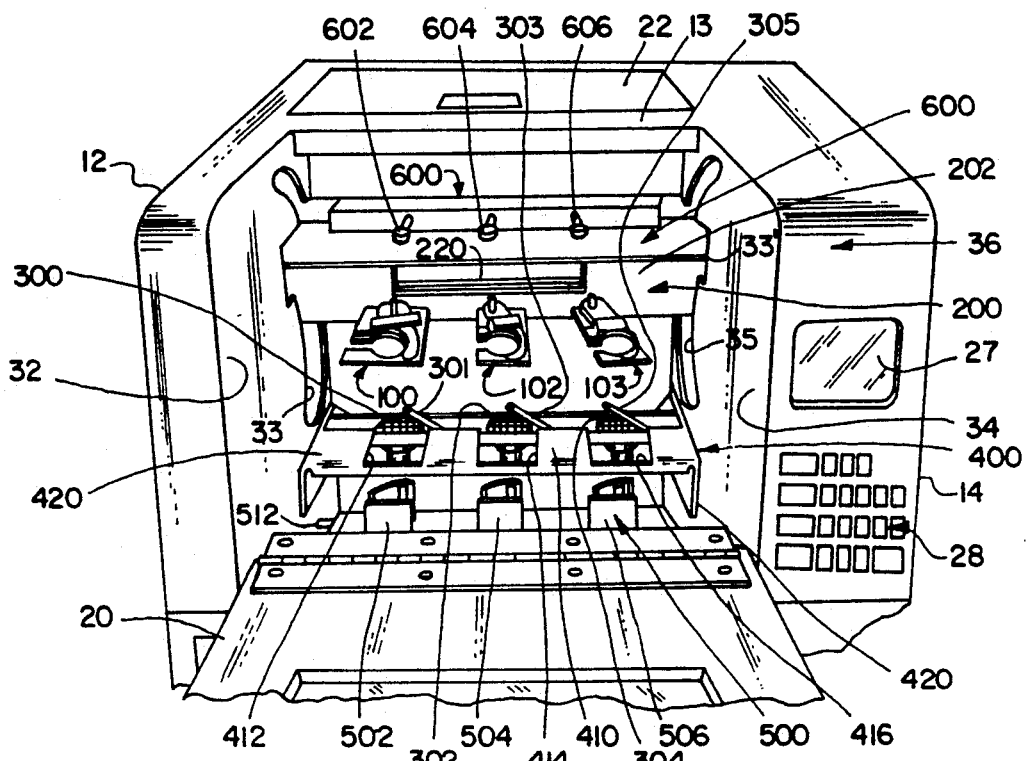
FIG. 2 is a front perspective view of a portion of the instrument shown in FIG. 1, showing the major constituent operational elements of the instrument.

Instrument 10 includes several assemblies, each with a particular interrelated function, and a brief description of the assemblies and their operation is now presented in conjunction with FIG. 2 followed by a detailed description of the structure and operation of each of the assemblies and finally a detailed description of an operating cycle of the instrument. Mounted within cabinet 10 is a pair of inner vertically extending left and right side heat shield panels 32 and 34 respectively extend upwardly from the base 24 of the instrument cabinet to define an opening 36 for the constituent elements of the sample preparation apparatus. The sample contacting portions of the assemblies of the apparatus are located primarily within recess 36 including three substantially identical crucible holders 100, 102 and 104 all of which are identical with one of the crucible holders shown in detail and described later in conjunction with FIGS. 15-17.

Figure 13:
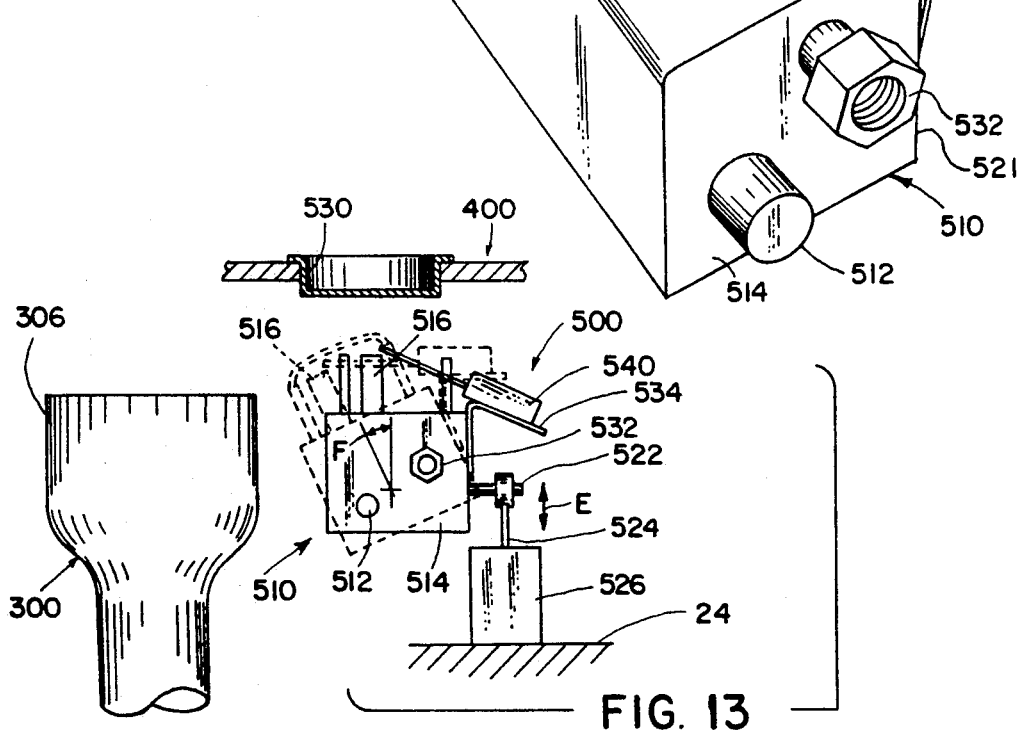
FIG. 13 is a left side elevational view partly in phantom form showing the relationship of the pilot burner assembly to one of the main burners and the casting dish assembly.
Figure 14:
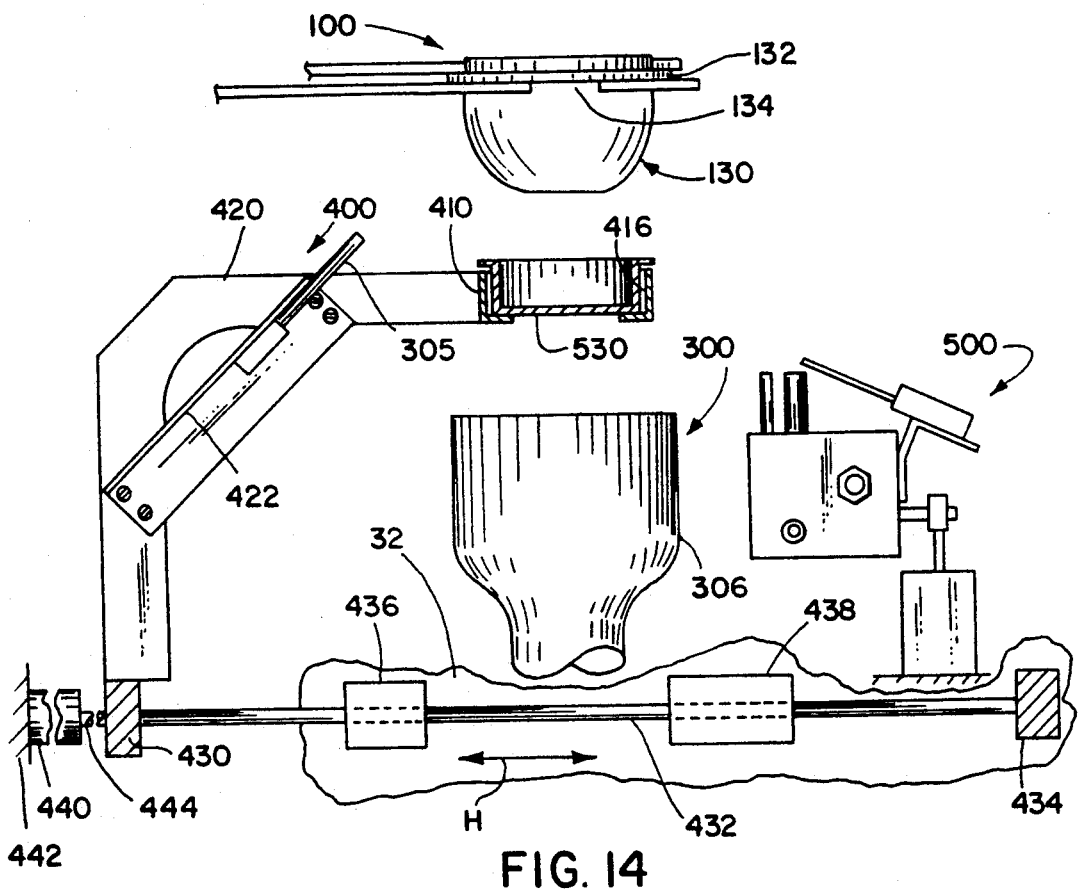
FIG. 14 is a fragmentary vertical cross-sectional view, partly broken away, of the casting dish assembly embodying the present invention.

Each of the crucible holders is removably mounted to a crucible agitation assembly 200 which provides independent X-Y motion to a crucible held within each of the crucible holders in vertical spaced alignment above three independent main burners 300, 302 and 304. The burners are mounted in fixed relationship to support base 24 of the instrument and are commercially available burners which are supplied, as described in greater detail below, with the combination of controlled compressed air and propane gas or other flammable gas to control the temperature of the burners as detected by thermocouples 301, 303 and 305 respectively. The thermocouples are mounted to a movable casting dish support assembly 400 which holds three casting dishes 530 (FIGS. 13-14) in spaced relationship with respect either to a burner or a pilot subassembly 500 positioned in the lower front of the recess 36 as seen in FIG. 2. Assembly 400 supports three shallow cup-shaped casting dishes above pilot burners 502, 504 and 506 respectively of pilot assembly 500 such that the pilot burner when not tilted rearwardly for lighting burners 300, 302 and 304 heats the casting dishes. Assembly 400 moves from a forward position shown in FIG. 2 to a rearward position over the main burners as seen in FIG. 14 for the casting of a sample melt from a crucible held in the crucible holders into the casting dishes as described in greater detail below.

In addition to the crucible holding and agitation assemblies, the casting dish assembly and the pilot assembly, the instrument also includes a nonwetting agent dispensing assembly 600 which includes three forwardly extending quartz scoops 602, 604 and 606. Assembly 600 moves between a forward position for loading, a subsequently retracted position during melting of the specimen, and again a forward position in which the scoops are rotated above a crucible adding a nonwetting agent to the melt prior to the casting operation. FIG. 2 shows the vertical spaced relationship of the various assemblies with the pilot assembly 500 being at the lowermost position, the burners 300, 302 and 304 being positioned above the pilot assembly but below the tray portion of the casting dish assembly 400; and the crucible agitation assembly 200 being located above the burners and the casting dish assembly 400. Finally, the nonwetting agent dispensing subassembly 600 is located above the crucible agitation assembly 200 with each of the assemblies being selectively movable in horizontal and/or vertical planes during various portions of each cycle of operation to selectively align with one another for providing their respective functions.

Figure 15:
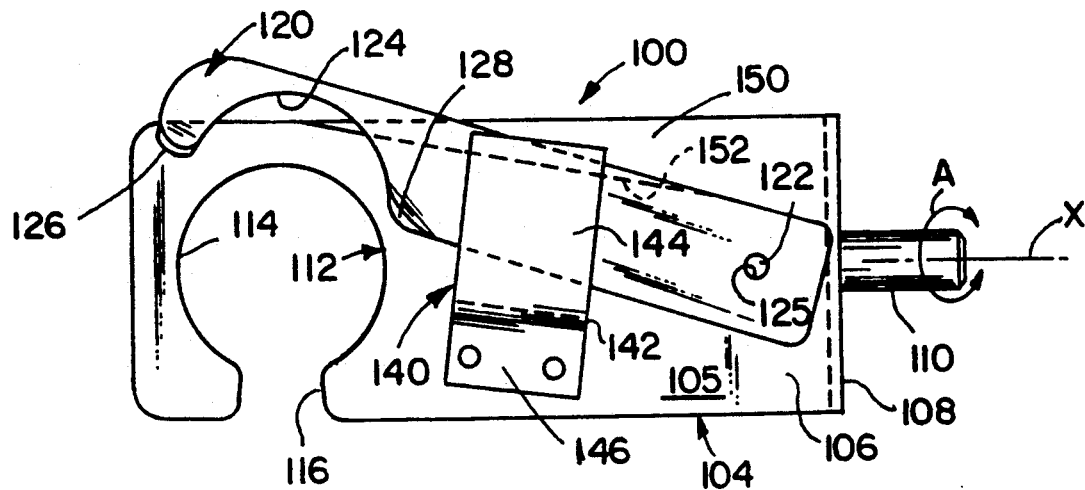
FIG. 15 is a top plan view of a crucible holder embodying the present invention.
Figure 16:
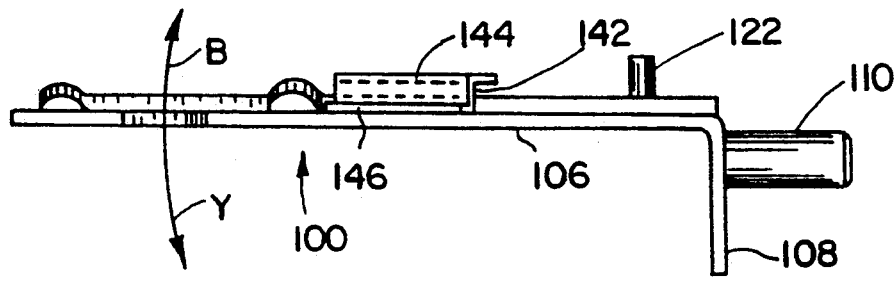
FIG. 16 is a front elevational view of the structure shown in FIG. 15.
Figure 17:
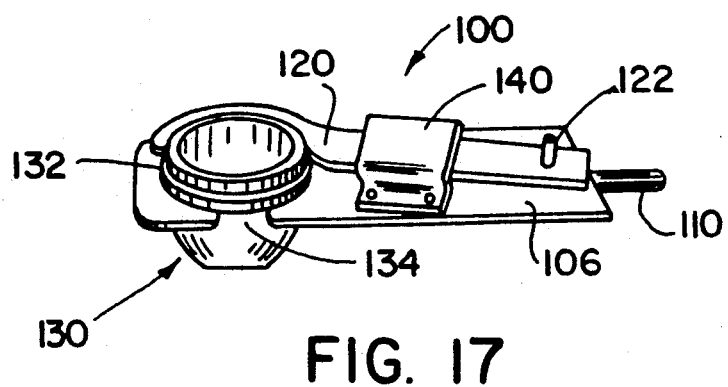
FIG. 17 is a perspective view of the structure shown in FIGS. 16 and 17 shown with a crucible positioned therein.

Before describing the agitation assembly 200 for the crucible holders, a brief description of the crucible holders which can be removably mounted to assembly 200 is presented in connection with FIGS. 15-17. Each of the crucible holders 100-102 are identical and a description of only crucible holder 100 is presented. Crucible holder 100 includes a first member 104 which is generally L-shaped including a flat-top plate 106 with a downwardly depending rear leg 108. Leg 108 includes a centered rearwardly extending mounting pin 110 which fits within assembly 200 for the removable mounting of each of the holders to assembly 200 as described below. The forward portion of plate 106 includes a generally circular opening 112 defining a rim 114 over which a protruding peripheral flange 132 of a platinum crucible 130 extends for support as best seen in FIG. 17 when a crucible is mounted within the crucible holder 100. Aperture 112 includes a laterally extending slot 116 formed therein which, as seen in FIG. 17, exposes an area 134 of the crucible. Just prior to pouring the sample melt from the crucible into a casting dish, holder 100 is tilted approximately 35° exposing the lip of the crucible in area 134 to the direct flame of the burner. This heats the upper rim of the crucible to prevent cooling in this area as the sample melt is poured into a casting dish. Slot 116 permits a direct flame to impinge upon the crucible for such purpose.

Each crucible holder includes a pivoted locking arm 120 which is pivotally mounted to plate 106 by an upwardly extending pivot pin 122 located near the rear of plate 106. Arm 120 is generally rectangular and includes a semi-circular recess 124 which extends over the rim 132 of crucible 130 for holding the crucible in position. A pair of upwardly extending tips 126 and 128 guide the pivoted looking arm 120 over the rim of the crucible once a crucible has been dropped into aperture 112.

The holder 100 also includes a guide plate 140 which is welded at an angle across the upper surface of plate 106 and includes a vertical wall 142 and an end section 144 which overlies arm 120 for holding the arm in position as the holder is rotated both during agitation and casting. Wall 142 elevates end 144 a sufficient distance to clear the upper surface of arm 120 as seen in FIG. 16. A rear flange 146 is suitably welded to plate 106. Arm 120 includes an aperture 125 sufficiently larger than pivot pin 122 to allow the arm to move relatively freely and be lifted out of the way for the insertion and removal of a crucible therein using tongs or other mechanical means. Member 140 suitably restrains the movement of the arm during the agitation and pouring functions to maintain the crucible in position. A triangular guide plate 150 is welded to the edge of plate 106 opposite flange 146 of member 140 to define a channel between the vertical member 142 of member 140 and the edge 152 of triangular plate 150 with the arm 120 in a locking position to hold the arm in a flush position against the top surface 105 of plate 106 as best seen in FIGS. 16 and 17.

The crucible holder connection to the agitation assembly 200 is through pin 110 with the agitation mechanism rotating the holder 100 around an X-axis in a direction indicated by arrow A in FIG. 15 in an oscillatory fashion and a vertical Y-axis shown in FIG. 16 as indicated by arrow B in this FIG. by the pivoting of the mechanism 200 as described below. Thus a crucible held in one of the crucible holders can move in a controlled fashion about the X-Y axes while at the same time the powdered sample material and flux is heated by burners 300, 302 and 304 to heat the melt contained therein to a temperature of about 645 degrees C. to 920° C. depending upon the sample and flux being used. As discussed above, the samples conclude a variety of silicon, aluminum, calcium, magnesium materials while the fluxes also can be a variety of different fluxes, each of which requiring a particular temperature which is controlled by controlling the flame temperature in a range of from about 1050° to 1400° C. described below. The flux use can be a lithium metaborate or lithium tetraborate for example which in connection with different samples provides a viscosity to the sample melt (i.e. the powdered sample and powdered flux in melted liquid state) requiring the different agitation rates and patterns provided by subassembly 200 which is now described in connection with FIGS. 2-6.

Figure 3:
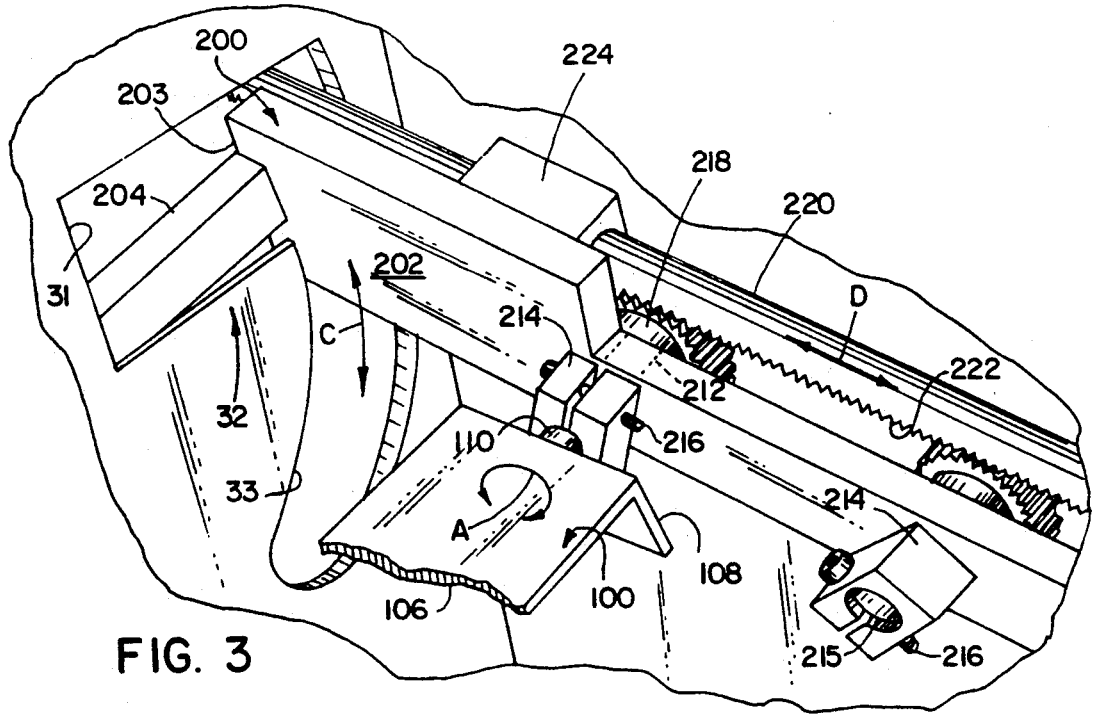
FIG. 3 is an enlarged perspective view of a portion of the crucible agitation structure shown in FIG. 2.

The agitation assembly 200 includes as best seen in FIGS. 2 and 3 a horizontally extending cross-member 202 having a first end 203 extending through an arcuate slot 33 in sidewall 32 (FIG. 4) and secured to an end of a pivot arm 204. Arm 204 is pivotally mounted to a vertically extending mounting plate 270 extending upwardly from base 24 by a pivot axle 206. The opposite end 207 of cross-member 202 extends through a similar arcuate slot 35 in wall 34 to form a mounting block for receiving the X-axis control motor 240 as seen in FIG. 5. The Y-axis control motor 230 is coupled to the pivot axis of a second pivot arm 208 (FIG. 6) which extends rearwardly behind motor 240 (as viewed in FIG. 5) to cross-member 202 and is secured thereto in a suitable fashion. Thus cross-member 202 is mounted for vertical arcuate movement in an arc shown by arrow C in FIGS. 4 and 5 by pivot arms 204 and 208.

Figure 4:
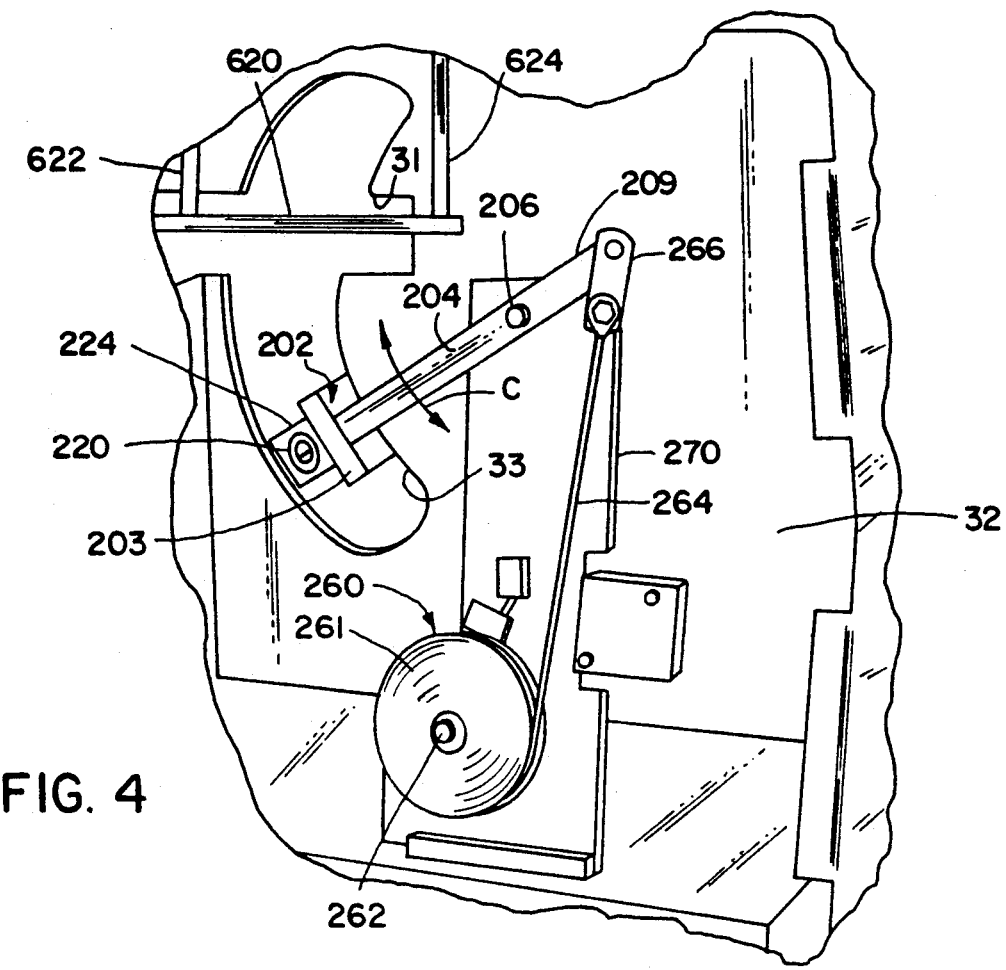
FIG. 4 is a left side elevational view of the instrument showing a portion of the agitation structure seen also in FIG. 3.
Figure 5:
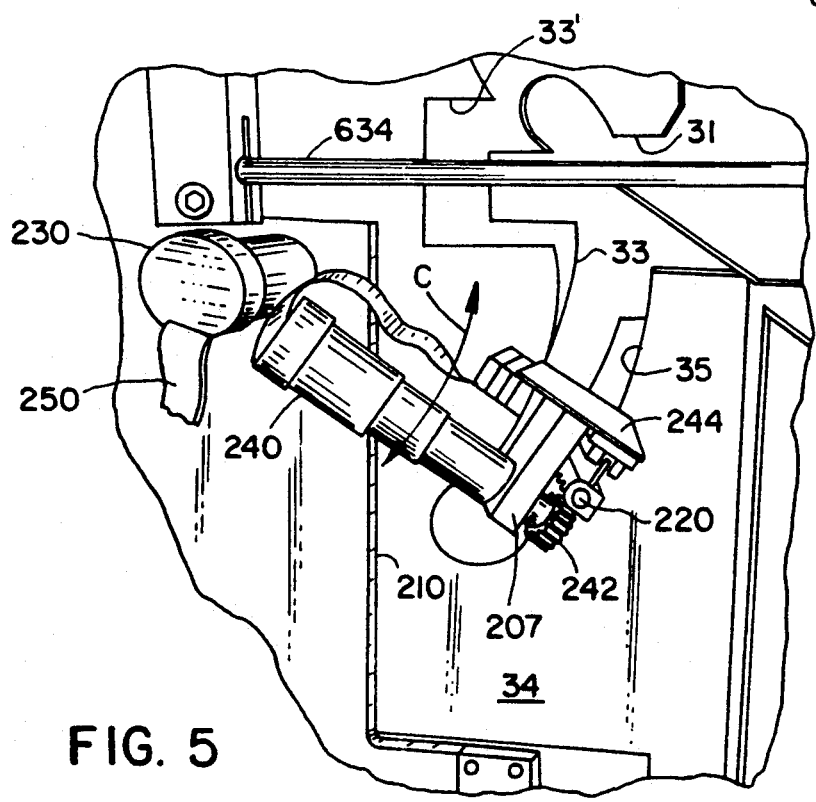
FIG. 5 is a right side elevational view of a portion of the agitation structure shown in FIGS. 2-4.
Figure 6:
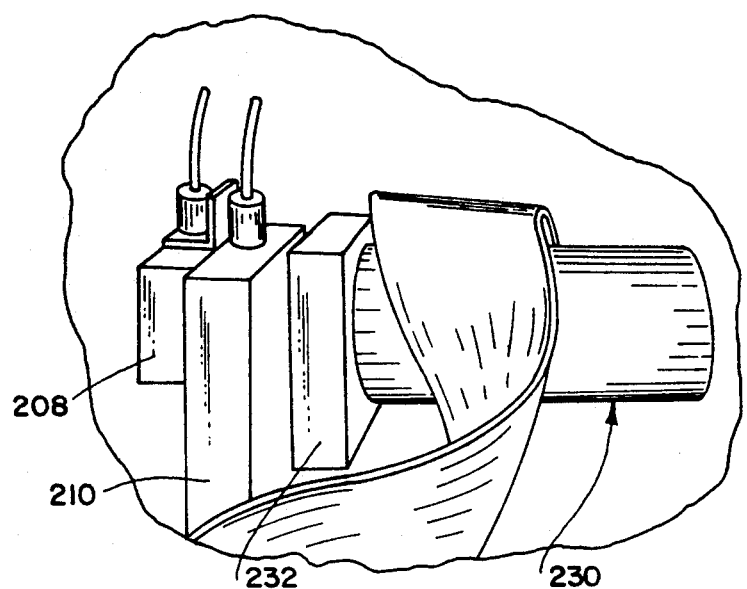
FIG. 6 is an enlarged fragmentary front perspective view of a portion of the structure shown in FIG. 5.
Figure 7:
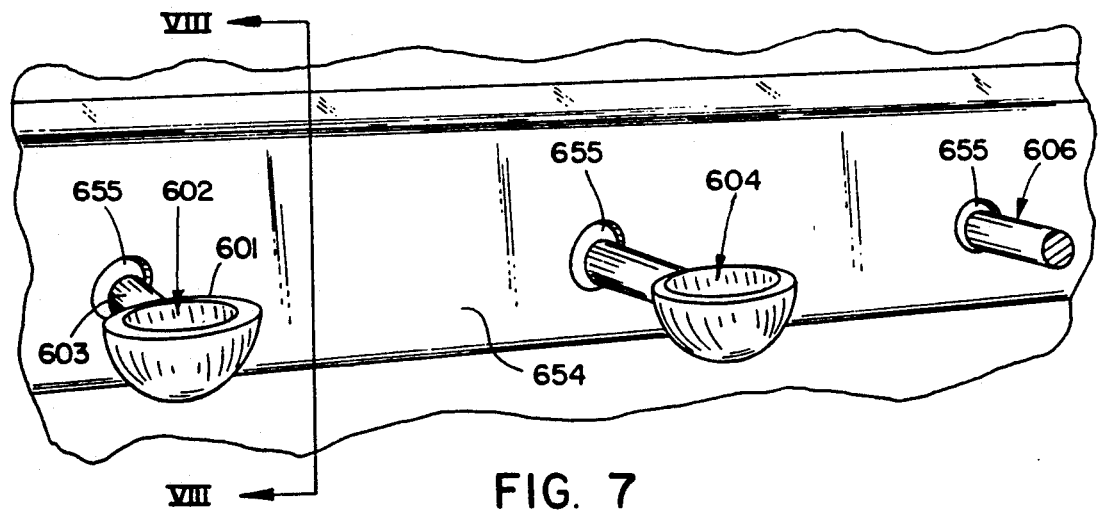
FIG. 7 is a fragmentary enlarged front elevational view of a portion of the nonwetting agent adding structure shown in FIG. 2.

The cross-member 202 is held at rest in a horizontal position by a spring-loaded counter spring assembly 260 shown in FIG. 4 which is mounted to a pivot axle 262 which has a coil spring mounted on a drum 26 rotatably mounted to an axle 262 secured to the vertical mounting plate 270. A cable 264 couples the end of the counterweight spring assembly 260 by a pivot mounting member 266 to end 209 of arm 204 such that the arm is at rest in a horizontal position as shown in FIG. 4 and during agitation is in either a lowered position as illustrated in FIG. 5 or a raised position near the upper end of the slots 33 and 35 through panels 32 and 34 respectively.

The drive motor to provide this Y-axis motion is mounted to a mounting plate 210 extending upwardly from the base 24 of instrument 10 to a mounting block 232. The shaft of motor 230 is directly coupled to the pivot axle of arm 208.

Figure 19:
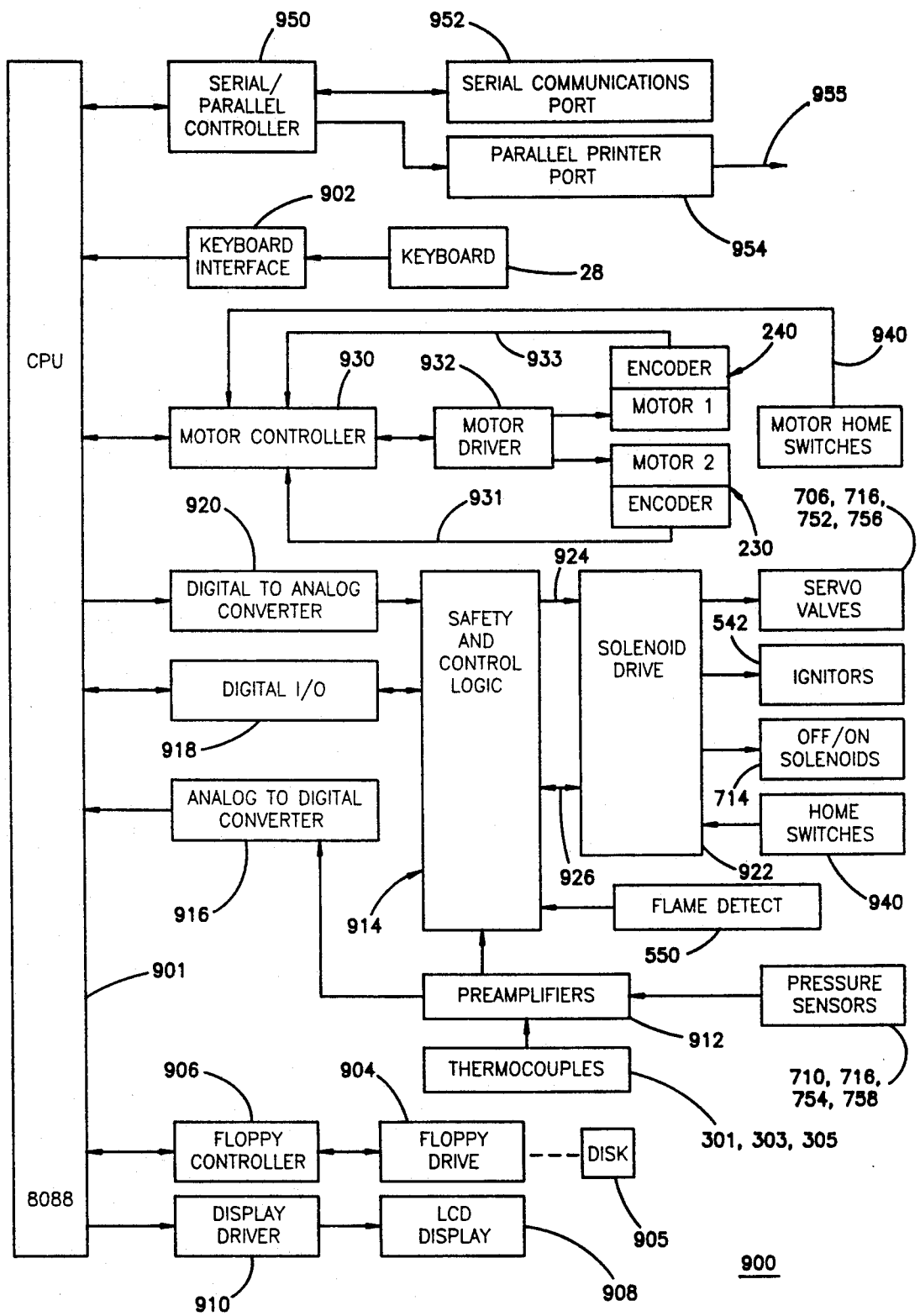
FIG. 19 is an electrical circuit diagram in block form of the electrical control system embodying the present invention.

Motors 230 and 240 are DC servo motors with optical shaft encoders built-in for providing position indicating signals to the computer control circuit shown in FIG. 19 to indicate the speed of and exact position of the shaft of each of the drive motors. Thus the exact speed of and the position of cross-member 202 is always known as is the speed of and angle of inclination of the crucible holder and crucible mounted thereto. FIG. 3 illustrates the mounting assembly for each of the crucible holders with holder 100 being partially shown. Extending through cross-member 202 are three apertures with aperture 212 being shown in FIG. 3. In each of the apertures there is mounted a sleeve-bushing 215 for receiving a split clamp 214 with a looking screw 216 for clamping the mounting pin 110 (FIGS. 15-17) of the crucible holder 100 to the sleeve-bushing which is rotatably mounted within apertures 212. Mounted on the rear side of cross-member 202 and to the bushing 215 is a rotatable gear 218 which engages the underside of a rack 220 having gear teeth 222 formed thereon.

Rack 220 is supported on opposite ends to cross-member 202 by means of a pair of spaced pillow blocks 224 such that it can slide laterally in the direction indicated by arrow D in FIG. 3 when driven by the X-axis motor 240. Thus lateral movement of the rack 220 rotates each of the gears 218 to which the bushings 215 are coupled and therefore the crucible holder 100 mounted thereto around the X-axis in a direction indicated by arrow A in FIGS. 3 and 15. Independently, while at the same time, the Y-axis motion of cross member 202 is achieved by the Y-axis motor 230 in a direction indicated by arrow C in FIGS. 3 and 5. The rack 220 is driven by a gear 242 on the shaft of motor 240 which is mounted to the end 207 of cross-member 202 as best seen in FIG. 5. Rotation of the gear 242 thereby causes the generally rod-shaped rack 220 to move in opposite directions along the axis shown by arrow D in FIG. 3, simultaneously rotating each of the three crucible holders 100, 102 and 104 in the same direction at exactly the same frequency and amplitude. The motor can move the rack a distance sufficient to invert the crucibles held within the crucible holders for the casting step as described below. A motor control circuit board 244 can be conveniently located on the upper edge of arm 202 as seen in FIG. 5 for containing the control circuit for both of the X-Y motors which are coupled to the motor control circuit and to the control circuit by suitable ribbon conductors 250.

By providing two independent drive motors 230 and 240 which are independently driven and controlled, independent oscillations in both the directions A and C (i.e. the X-Y axes respectively) can be achieved. The amplitude and frequency of these oscillations can be controlled independently as described in greater detail below as can the ratio of the amplitudes and speeds to achieve any desired agitation pattern for a particular sample melt to achieve homogeneity of the mix of sample and flux at the earliest time.

As noted above, various agitation patterns such as a W-pattern, an hourglass pattern, a figure-eight pattern or any other elliptical, circular or other pattern can be achieved by the independent X-Y motor control of the assembly 200 to which the crucible mounts are attached. The frequency of the motor controls can range from 10 to 90 cycles per minute and the X-Y axes rotations are from plus or minus 5° to 30°. Also, the ratio of the number of cycles of X rotation compared to the number of cycles of Y rotation can be varied from 1:1 to approximately 1:5 such that the X rotation can be 5 times faster than the Y rotation if desired. Thus a substantial finite number of agitation controls can be provided by assembly 200 with the DC servo control motors 230 and 240 being independently controlled by the control circuit of FIG. 19.

Figure 12:
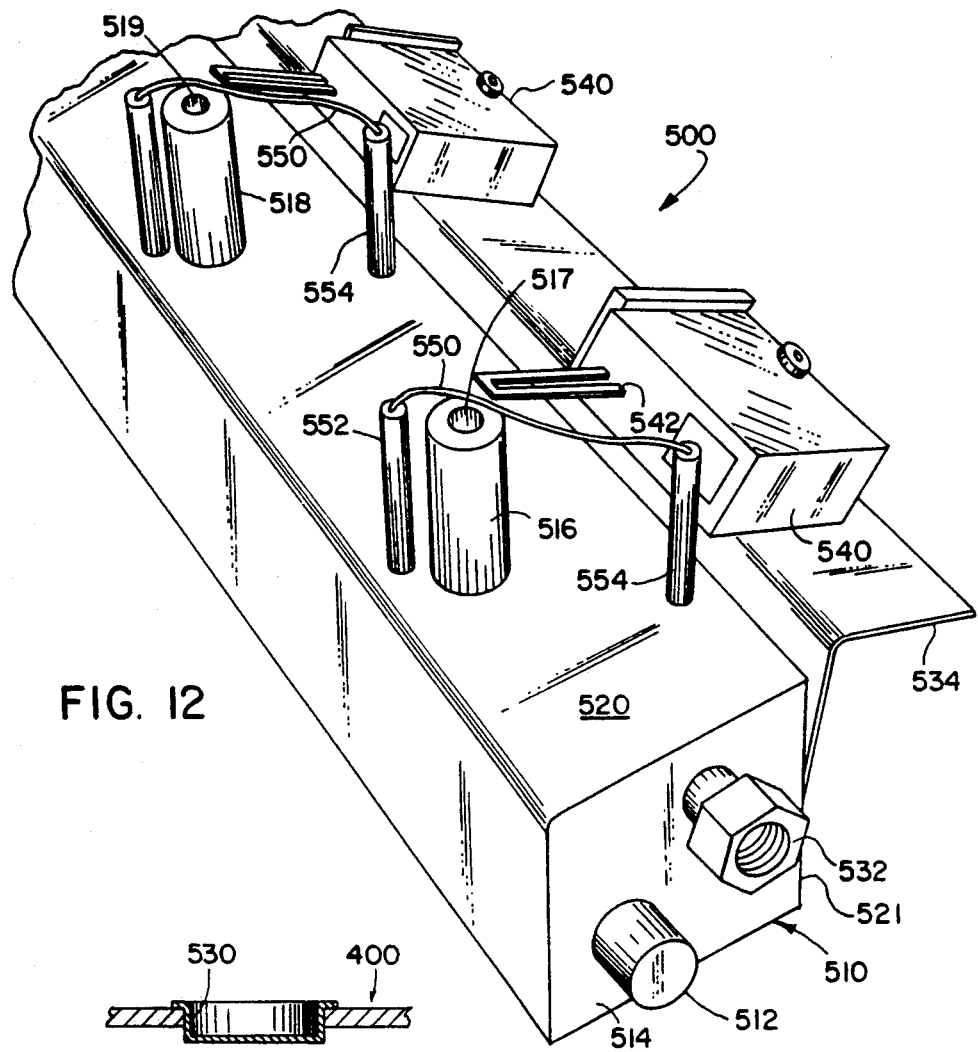
FIG. 12 is a fragmentary perspective view of a pilot burner assembly embodying the present invention.

Each of the burners 300, 302 and 304 is supplied with a source of compressed air and gas mixture as illustrated by the flow diagram of FIG. 18 and described below. Each of the burners is mounted to the base 24 and includes a burner head 306 (FIG. 14) which is located in vertical alignment below a crucible 130 positioned in a crucible holder 100. Each of the burners is ignited by the pilot assembly 500 which serves the dual function of also heating the casting dishes. Turning now to FIGS. 12 and 13, a description of the pilot assembly 500, also shown in FIG. . 2, is presented.

The pilot burner assembly 500 comprises a generally rectangular hollow manifold 510 as best seen in FIG. 12 with a pivot rod 512 extending from opposite ends of end walls 514 of manifold 510 for pivot mounting the assembly 500 to the sidewalls 32 and 34 of the instrument. The view of FIG. 12 is a rear left corner view showing a pair of burner heads 516 and 518 extending upwardly from the top wall 520 of manifold 510. Along the forward wall 521 of manifold 510 there extends a central pivot pin 522 which is coupled to the shaft 524 of pneumatically controlled cylinder 526 by means of a suitable clevis coupling. Shaft 524 moves upwardly and downwardly in a direction indicated by arrow E (FIG. 13) for pivoting the pilot burner assembly 500 about the pivot axles 512 in a direction indicated by arrow F in FIG. 13.

When cylinder 526 is activated to move shaft 524 outwardly from the body of the cylinder, the pilot assembly tilts rearwardly, as viewed in FIG. 2, to a position shown in phantom lines in FIG. 13. This positions each of the burners such as burner 516 above and adjacent the head 306 of burner 300 for example, for igniting the burner in a controlled fashion. Once ignited and the thermocouples (301, 303 and 305) detect a flame, the cylinder 526 is actuated to tilt forwardly in a position shown in solid lines in FIG. 13 to a position below a casting dish 530. A combustion gas such as propane together with compressed air are fed to the manifold 510 through conduits coupled from sources 701 and 703 (FIG. 18) of such gases respectively, to fittings 532 on opposite ends of end walls 514 of the manifold and communicate with the interior of the manifold for controlling the supply of compressed air and combustion gas to the pilot burners therein. By supplying gas at opposite ends to the manifold, using suitable flexible conduits to accommodate the rotation of the pivot burner assembly; a mixture of the gas and compressed air takes place due to the impingement of the gases coming from opposite ends of the manifold.

A mounting flange 534 extends downwardly and forwardly of the manifold 510 and supports thereon an ignition member 540 having an electrically controlled ignitor element 542 which extends immediately adjacent the ends of each of the nozzles 516 and 518 near the orifices 517 and 519 respectively for providing an ignition temperature sufficient to ignite gases flowing from the pilot nozzles. The existence of a pilot flame is detected by platinum wire 550 which is mounted in spaced insulative relationship to the upper wall 520 of the metallic burner assembly 500 by means of insulating posts 552 and 554. The platinum wire is coupled to the control oircuit and detects the existence of a flame from each of the burners by determining the resistance of wire 550 to ground to provide a safety control signal indicating whether or not each of the pilots embodied in the instrument is ignited after an ignition signal has been sent to the ignitor assemblies 540 and the gas control valves as discussed below.

With the burners ignited and the agitation assembly 200 activated, the crucibles are heated to provide the desired sample melt. Before casting the melt into the casting dishes 530, a nonwetting agent is dispensed by the dispensing assembly 600. In the preferred embodiment of the invention, the nonwetting agent comprises a powdered material such as lithium iodide (LiI) which is placed in the quartz scoops 602, 604 and 606 of the three burner instrument 10 as shown in FIGS. 2 and 7-11. This structure is now described in greater detail.

Figure 10:
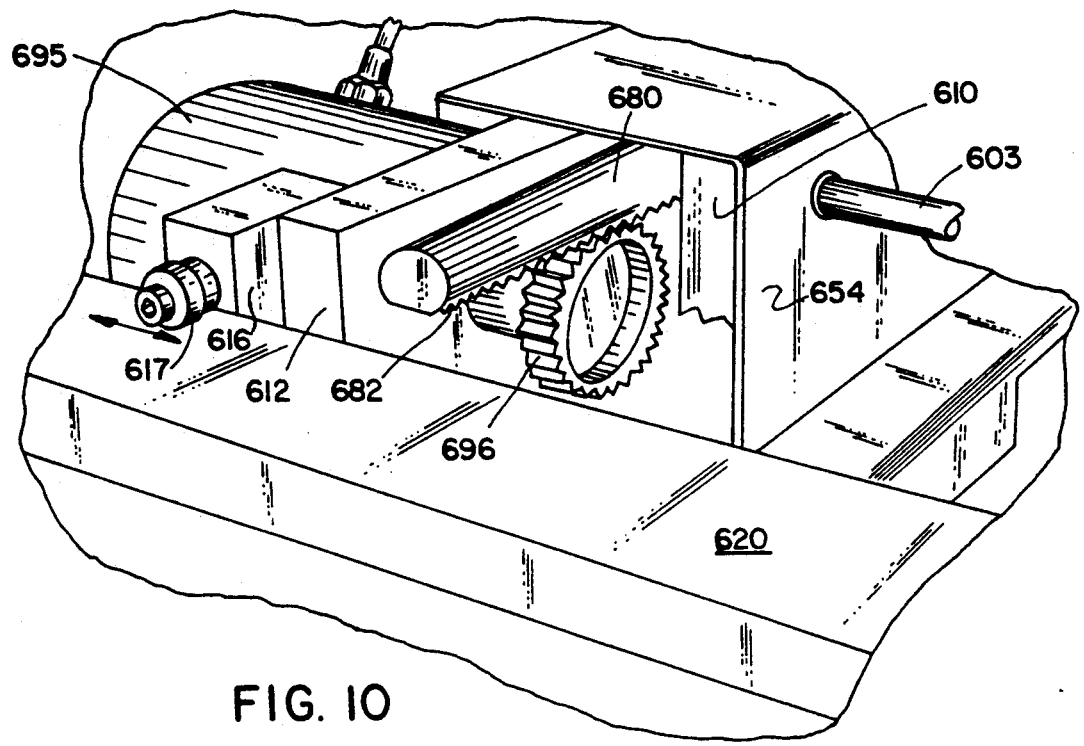
FIG. 10 is a left end fragmentary perspective view of the drive structure for the dispensing structure shown in FIGS. 7-9.
Figure 11:
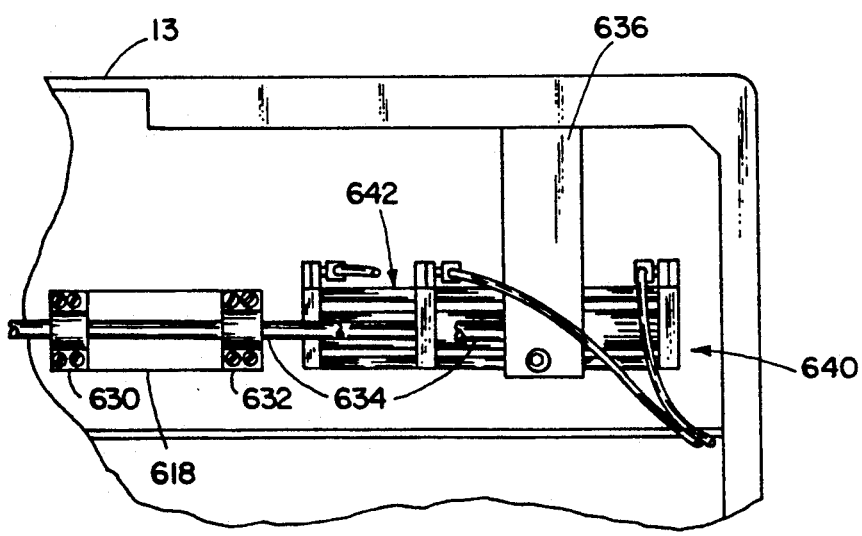
FIG. 11 is a fragmentary right side elevational view of the structure shown in FIG. 9.

The dispensing assembly 600 for the nonwetting agent includes a pair of cross-members 610 and 612 (FIG. 8) which extend through rectangular slots 31 and 33 (FIGS. 4 and 5) in sidewalls 32 and 34 respectively of the instrument. Cross-members are horizontally spaced from each other and terminate, as seen in FIGS. 10 and 11, on slide members 616 and 618 respectively. As best seen in FIG. 10, the left side of the instrument includes slide member 616 with upper and lower roller followers 617 which span a flat horizontally extending rectangular slide bar 620. Bar 620 is suspended by a pair of support rods 622 and 624 (FIG. 4) suitably mounted to the cabinet to allow the cross-members 610 and 612 to move forwardly and rearwardly with respect to the instrument, as viewed in FIG. 2. The right end of the instrument includes the slide member 618 which is supported by a pair of spaced pillow blocks 630 and 632 for fore and aft guided movement on a guide rod 634 suitably supported in the cabinet by means of spaced mounting blocks suitably mounted to the cabinet at opposite ends of rod 634. The rear mounting block 636 is illustrated in FIG. 11.

Figure 8:
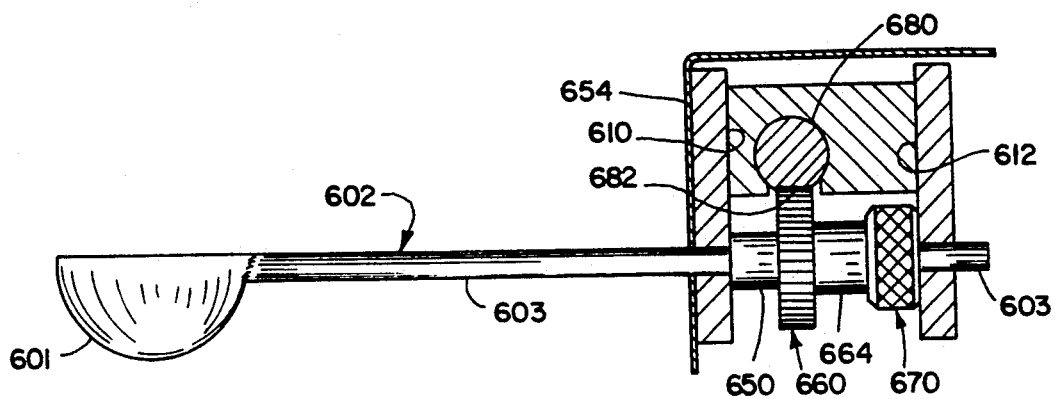
FIG. 8 is a cross-sectional view taken along section lines VIII—VIII of FIG. 7.

The fore and aft motion of the dispensing assembly 600 is achieved by a pair of serially stacked cylinders 640 and 642 (FIG. 11) with the rearward cylinder 640 being mounted to the cabinet and to an intermediate plate to which the forward cylinder 642 is mounted and having its shaft coupled to the rearwardmost cross-member 612 of assembly 600. Thus, actuation of cylinders 640 and 642, which doubles the throw or distance of travel of approximately 10 inches of assembly 600, provides for a compact instrument case which allows sufficient movement of the dispensing assembly cross-members to achieve the desired fore and aft motion. The dispensing assembly is moved forward during initial loading and during the actual dispensing operation. Thus during the majority of the cycle of operation of the instrument, the dispensing assembly is in its rearwardmost position. The dispensing of powdered nonwetting agent from the scoops 602, 604 and 606 is achieved by the axial rotation of each of the scoops along the longitudinal axis of their integral support rod 603 by the structure as best seen in FIGS. 8 and 9 driven by a rack motor assembly best seen in FIG. 10.

Figure 9:
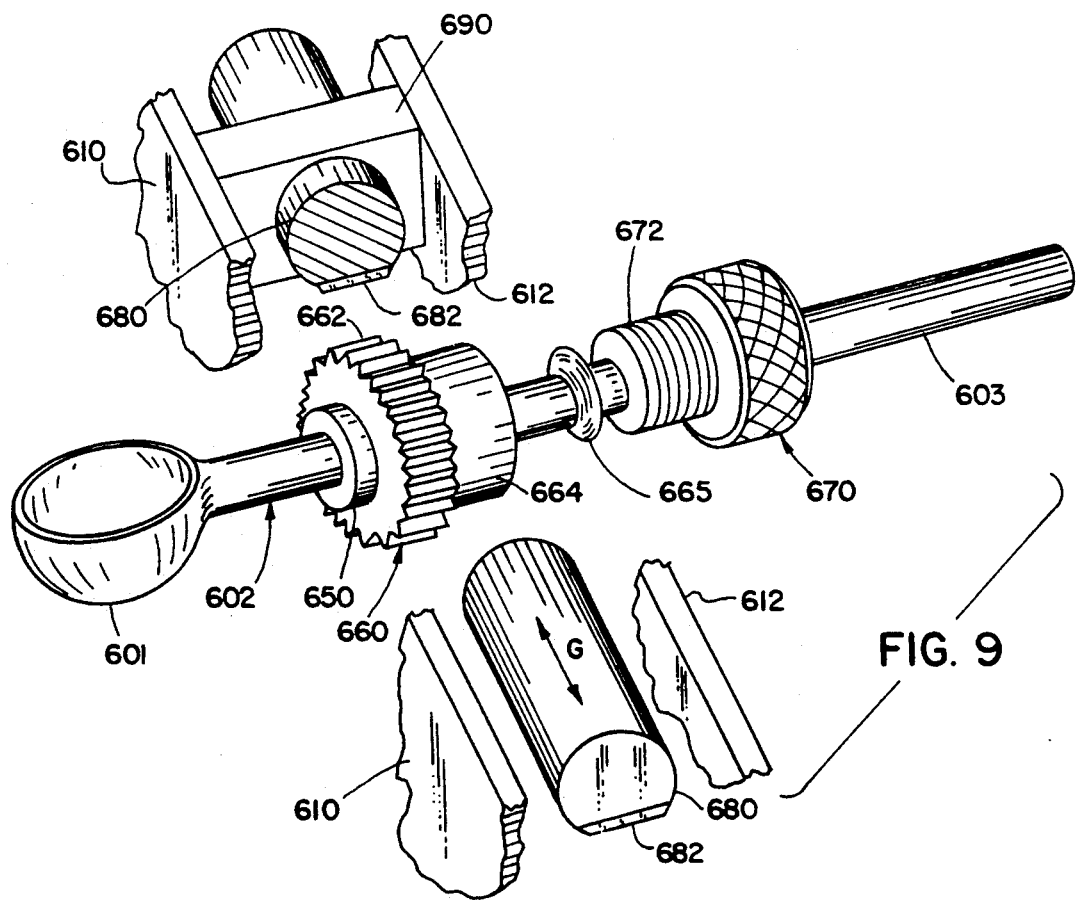
FIG. 9 is a exploded perspective view, partly broken away and in fragmentary form, of one of the dispensing elements shown in FIGS. 7 and 8.

Referring initially to FIG. 9, there is shown one of the dispensing members 602 which includes a cup-shaped scoop 601 at one end which is mounted to a rearwardly extending rod 603. Rod 603 extends through apertures formed through the forward and aft cross-members 610 and 612 and uniquely serves as the mounting axles for the gears which rotate the scoops. A cylindrical spacer bushing 650 (FIGS. 8 and 9) extends over rod 603 followed by a gear 660, a compression ring 665 in the form of an O-ring which snuggly fits around the rod 603 and is held within gear 660 by a knurled locking nut 670. Follower gear 660 includes an axial extending aperture formed therein and an outer periphery with gear teeth 662 extending therearound and which fits under and mateably engages teeth 682 on a gear rack 680. Rack 680 is mounted for lateral movement as indicated by arrow G in FIG. 9 by a pair of spaced pillow blocks 690 mounted between cross-members 610 and 612.

Each of the gears 660 includes a rear cylindrical section 664 having a threaded aperture for receiving the threaded shaft 672 of locking nut 670 and an O-ring seat at its inner end for receiving compression member 665 held within cylindrical section 664 and compressed by nut 670 when tightened to grip rod 603 and yet allow removal of the scoops and gears by withdrawing them from the front of cover 654. Thus the rotation of each of the follower gears 660 associated with each of the dispensing scoops 602, 604 and 606 is achieved by the linear motion of rack 680 driven by a drive motor 695 (FIG. 10) mounted to the rear plate 612 with its drive gear 696 engaging teeth 682 of rack 680 as best seen in FIG. 10. Drive motor 695 is a pneumatically driven rotary cylinder which rotates the drive gear 696 sufficiently to invert the scoops 602, 604, 606 to dump the measured nonwetting agent into the open mouth of the crucibles 130 when the assembly 600 is moved toward its forward position with the scoops aligned directly over the open mouth crucibles. A protective L-shaped cover 654 extends over the front of front cross-member 610 the top area between members 610 and 612 to provide a protective cover for the rack 680. Plate 654 includes suitable apertures 655 through which the shafts 603 of the dispensing scoops extend.

Thus with the dispenser system of the present invention, a powdered nonwetting agent can be dispensed at the time desired over the 1300° C. flame of the burners without operator interaction and automatically when desired. When the melt has homogenized at the end of an agitation cycle, the nonwetting agent is added to the crucible, and the pouring and casting operation takes place utilizing the casting dish assembly 400 shown in FIGS. 2 and 14.

The casting dish assembly 400 moves only in a fore and aft direction to place a plurality of casting dishes 530 over either the pilot burner as shown in FIG. 13 or over the main burner for pouring as shown in FIG. 14. The casting dish assembly includes a horizontally and laterally extending table 410 with, in the preferred embodiment, three circular apertures 412, 414 and 416 for receiving therein either the casting dishes 530 directly or a removable tray for receiving three of the casting dishes which can be simultaneously lifted from the table 410. The table extends between opposite ends of a pair of inverted reversed L-shaped end supports 420 with one end support being located at each end of the table in inner spaced relationship between the sidewalls 32 and 34 of the instrument. Extending between the end L-shaped members is an inclined plate 422 to which the thermocouples 301, 303 and 305 are mounted such that when the assembly 400 is moved forwardly (to the right from the position shown in FIG. 14) the thermocouple 305 will be directly over the burner head 306. In this position, apertures 416 of the table 410 will be forwardly of the burner and in a position shown in FIG. 2.

The L-shaped legs 420 extend downwardly as best seen in FIG. 14 terminating in a lower cross-member 430 which is coupled to a forward cross member 434 by a pair of slide rods 432 with one extending between each end of the cross-members 430 and 434. Each of the guide rods 432 is slideably mounted to pillow blocks 436 and 438 mounted on sidewalls 32 and 34 of the instrument in spaced horizontal relationship to guide the assembly 400 in its fore and aft generally horizontal motion.

A cylinder 440 mounted to the cabinet as shown schematically at 442 includes a shaft 444 coupled to rear cross-member 434 providing fore and aft motion of the member 400 as shown by arrow H in FIG. 14. In the position shown in FIG. 14 the assembly is retracted rearwardly (i.e. to the left in FIG. 14) such that the casting dishes 530 are positioned directly below the crucible 130. In this casting position the agitation assembly 200 is controlled to first tilt the crucibles 130 approximately 35° to heat the area 134 of the crucible and subsequently and gradually invert the crucibles to pour the sample melt with the nonwetting agent previously added thereto into each of the casting dishes associated with each of the crucibles. When this is achieved, the casting dish holder assembly is moved forwardly again under the pilot burner assembly 500 where the dishes are cooled by turning off the pilot and main burners and applying only a controlled amount of compressed air to the pilot burners for directing a stream of compressed air to the bottom of the sample casting dishes as seen in solid lines in FIG. 13 for cooling the samples in a controlled fashion in the sample dishes. A substantially disk-shaped glass-like sample results from this solidification of the sample melt which can be removed from the sample dish and subsequently analyzed by any number of analytical techniques such as X-ray fluorescence spectroscopy. Having described the mechanical elements making up the various assemblies of the system of the present invention, a brief description of the gas flow path and control elements is presented in connection with FIG. 18.

Figure 18:
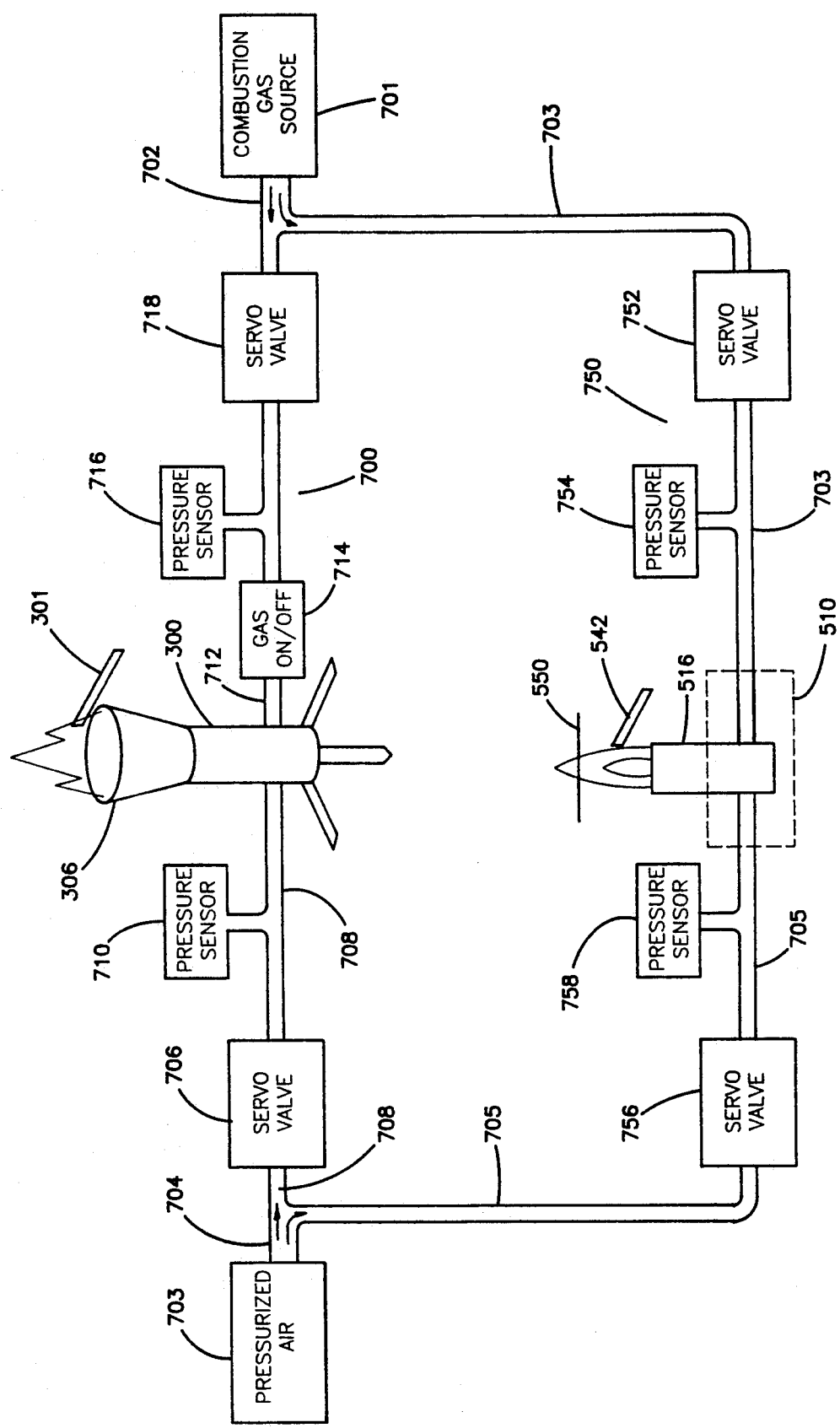
FIG. 18 is a schematic diagram of the gas and air flow paths for one of the burner assemblies and the pilot assembly embodying the present invention.

Referring now to FIG. 18, there is shown the gas flow system for the instrument of the present system. Illustrated in FIG. 18 is only one of the three main burner legs which is identified as the upper flow path 700. It is to be understood that three identical flow paths and control elements are employed with one for each of the main burners 300, 302, and 304. A lower flow path 750 is provided for manifold 510 and three of the ignitor burners 516 being thereon with only one of the burners 516 being illustrated for purposes of the schematic diagram. On each of the legs 700 associated with each of the burners, a supply 701 of gas such as propane is coupled to inlet means 702 for supplying gas to the system. The pressure of propane is supplied through a propane tank with a regulator such that the pressure is approximately 20 PSI. Similarly, on the opposite end of gas flow leg 700 there is a source 703 of compressed air at approximately 40 PSI coupled to an inlet 704 consisting of means for applying a source of compressed air to the system. The compressed air is applied to each of the burners, such as burner 300 through a servo control proportional valve 706 coupled in series in a gas conduit 708 which includes a pressure sensor 710 for determining the pressure of the gas applied to the burner. The servo valve 706 is controlled by a solenoid drive circuit included in the electrical control circuit of FIG. 19. Each of the burners also receives the combustion gas through a conduit 712 including a series gas on-off valve 714 controlled by a control oircuit and which also includes a pressure sensor 716. Gas is supplied to the burner 300 through a servo control valve 718 coupling the gas inlet 702 to the burner through the main on-off valve 714. It is noted that each of the burners 300 separately include the elements 708–718 for individually controlling burners during the melt process to control the flame temperature very precisely for each of the burners.

The gas and air inlets 702 and 704 are also coupled to the manifold 510 of the pilot assembly 500 by gas conduits 703 and 705 respectively. The gas is supplied to the manifold through a servo valve 752 in series with conduit 703 and a pressure sensor 754 for determining the pressure of combustion gas supplied to the manifold 510. Similarly the compressed air is supplied through conduit 705 through a servo valve 756 to manifold 510. A second pressure sensor 758 monitors the pressure of compressed air applied to the manifold which is controlled as is the gas by the linear proportional servo valves to provide an exact flow of gas or air to the burner system shown in FIG. 18.

The various electrically controlled servo valves motors and other electrical components are controlled by the electrical control circuit 900 shown in FIG. 19. The various elements previously described carry the same reference numeral as that previously identified and include the motors, servo valves, solenoid valves, thermocouples and the like. The heart of the control circuit 900 is a microprocessor (CPU) 901 which can be an Intel 8088 or its equivalent. Coupled to the CPU is the digital keyboard 28 including a numeric keypad and other digital input switches coupled to a keyboard interface circuit 902 to an input port 30 for the CPU 901. A floppy disk drive such as a 3-½ inch high-density drive 904 is also coupled to the CPU through a controller circuit 906. The disk drive receives one or more diskettes having the program contained therein for operation of the instrument. The program is described in greater detail in connection with the program flow diagram of FIGS. 21A–21J described below. The instrument further includes a LCD display 908 for displaying operational and control prompting information to the operator. Display 908 is coupled to the CPU 901 through a display driver circuit 910.

The thermocouples and pressure sensors are coupled by an analog preamplifier 912 to a safety control and logic circuit 914 which includes a plurality of comparator circuits with threshold level setting inputs for detecting over and under temperature conditions of the various burners and provide suitable safety control circuits such that in the event ignition does not take place, for example within a predetermined time, the ignitors are turned off and a suitable display message presented to the operator. This circuit can be of conventional design such as that used in solid state home furnaces for example. The preamplifiers 912 for the temperature and pressure input sensors are coupled to the CPU 901 through an analog-to-digital converter oircuit 916 for providing the same information to the CPU. The CPU also communicates, through the logic circuit 914 and a digital input/output circuit 918 and a D/A converter 920, control signals to and from the solenoid drive circuit 922 by an output bus 924 and an input bus 926. The flame detector 550 is also coupled to the logic circuit 940 by a suitable conductor to indicate whether or not the pilot flame has been detected.

The CPU also provides control signals depending on the program input information to a motor controller circuit 930 which receives motor speed and rotational position information from the optical encoders which are integral with motors 230 and 240 through input conductors 931 and 933 respectively and provides output control signals to a motor driver circuit 932 which is a solid state power control circuit providing power to activate motors 230 and 240. Positioned at the end of travel of the various movable elements to indicate the home position, for example cross arm 202 of the crucible agitation assembly 200 are a plurality of home switches indicated by block 935 which provide digital input signals through the motor controller 930 to CPU 901. Similar home position switches 940 for the valves are coupled by the solenoid drive circuit 922 and the logic circuit 914 to the CPU for providing information indicating the home position of such elements for reference purposes.

The CPU is also coupled through a controller circuit 950 to a serial communications port 952 and a separate parallel printer port 954 such that a data printout can be provided for parameters which represent a cycle of operation of the instrument. Circuit 952 allows the control circuit to communicate with other external peripheral devices. Printer port 954 may be coupled through an output conductor 955 to a suitable conventional printer.

The operation of the CPU in providing signals to the various elements such as the motors and valves in response to received information from the various sensors, is controlled by the program for the unit which, although unique to this application, is conventional in methodology. The program provides control signals for the CPU to sample incoming data and provide output control signals in response thereto in a sequence of operations according to a cycle of operation. Before describing the program elements which are represented by the program flow diagram of FIG. 21, a brief description of the overall operation is presented in connection with the flow diagram for the method of use of the instrument 10 presented in connection with FIG. 20.

Figure 20:
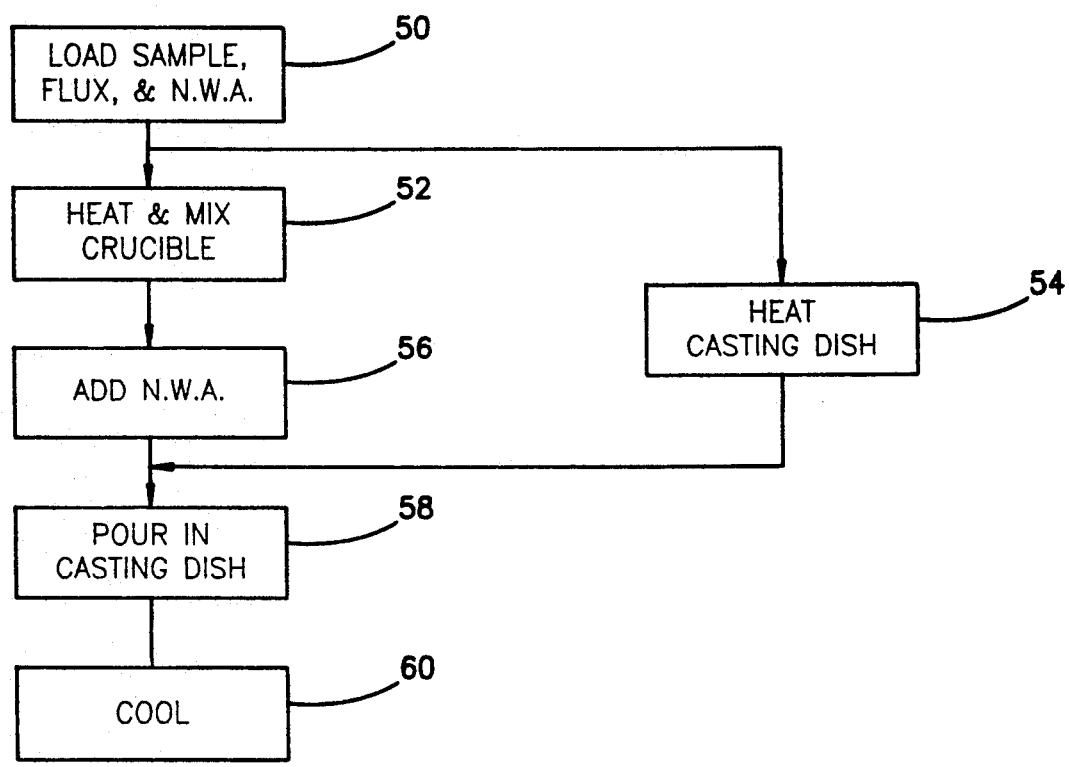
FIG. 20 is a flow diagram of the method of the present invention showing the sequence of operation of the instrument shown in FIGS. 1-19.

FIG. 20 shows the manual loading of a pre-measured sample and pre-measured flux as indicated by block 50 into crucibles 130. The manual loading step also encompasses the loading of a nonwetting agent in each of the scoops 602, 604 and 606 for the three burner version of the instrument with the dispensing assembly 600 being extended in its forwardmost position. Subsequent to the loading of the powdered material into the unit, the heating and mixing cycle is initiated in which the main burners 300, 302 and 304 are ignited by assembly 500 to apply heat to the crucibles 130 contained in the crucible holders 100, 101 and 102 as indicated by block 52 while at the same time the motors 230 and 240 are driven in a predetermined pattern for agitating the mix as the mix is heated for a predetermined period of time. At the same time, as indicated by block 54, the casting dishes placed in the assembly 400 are located directly over the pilot burners 502, 504 and 506 which heat the casting dishes to approximately the same temperature as the crucibles 130.

As the agitation and heating cycle times out, the nonwetting agent is added as indicated by block 56 by the actuation of assembly 600 to extend the scoops forwardly and over the crucibles and subsequently rotate the scoops to dump the powdered nonwetting agent directly into the crucibles. Subsequently, assembly 600 is retracted and the agitation is continued and the crucible holder is rotated 35° for a short period of time over the burners for heating the pouring lip area 134 of the crucibles. Next, the casting dish assembly 400 is retracted into a position illustrated in FIG. 14 to place the casting dishes directly under each of the crucibles 130 and above the main burners 300 which are now deactivated. The X-axis motor is controlled to pour the sample melts into awaiting casting dishes. These steps are illustrated by block 58 in FIG. 20. Finally, the assembly 400 is moved to its forwardly extended position as indicated by block 60 over the pilot burners to provide either heating or cooling using compressed air only for the controlled cooling of the sample melt to prevent its undesired thermal shock and cracking of the melt as it solidifies into a glass-like disk. Once the sample melt is cooled, the door 20 of the instrument can be opened and the sample dishes removed for the subsequent removal of the disk-shaped sample for analysis. The crucibles can also be removed for refilling. Having briefly described the overall system operation, a more detailed description of a cycle of operation under the computer program is now presented in conjunction with FIGS. 21A–21J.

Figure 21A:
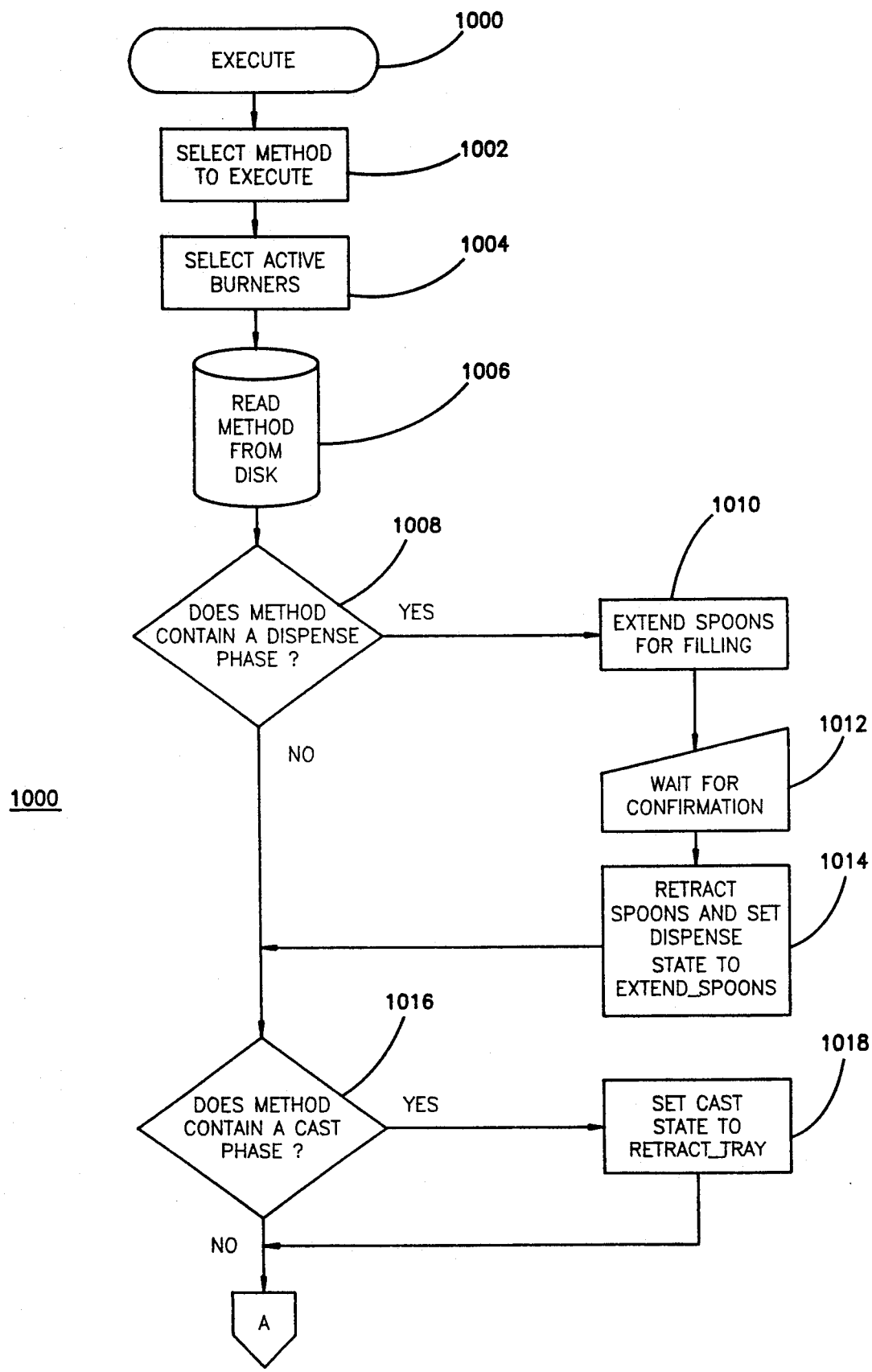
FIGS. 21A-21J is a flow diagram of the program used to control the microprocessor used in the electrical control system for the instrument of the present invention.
Figure 21B:
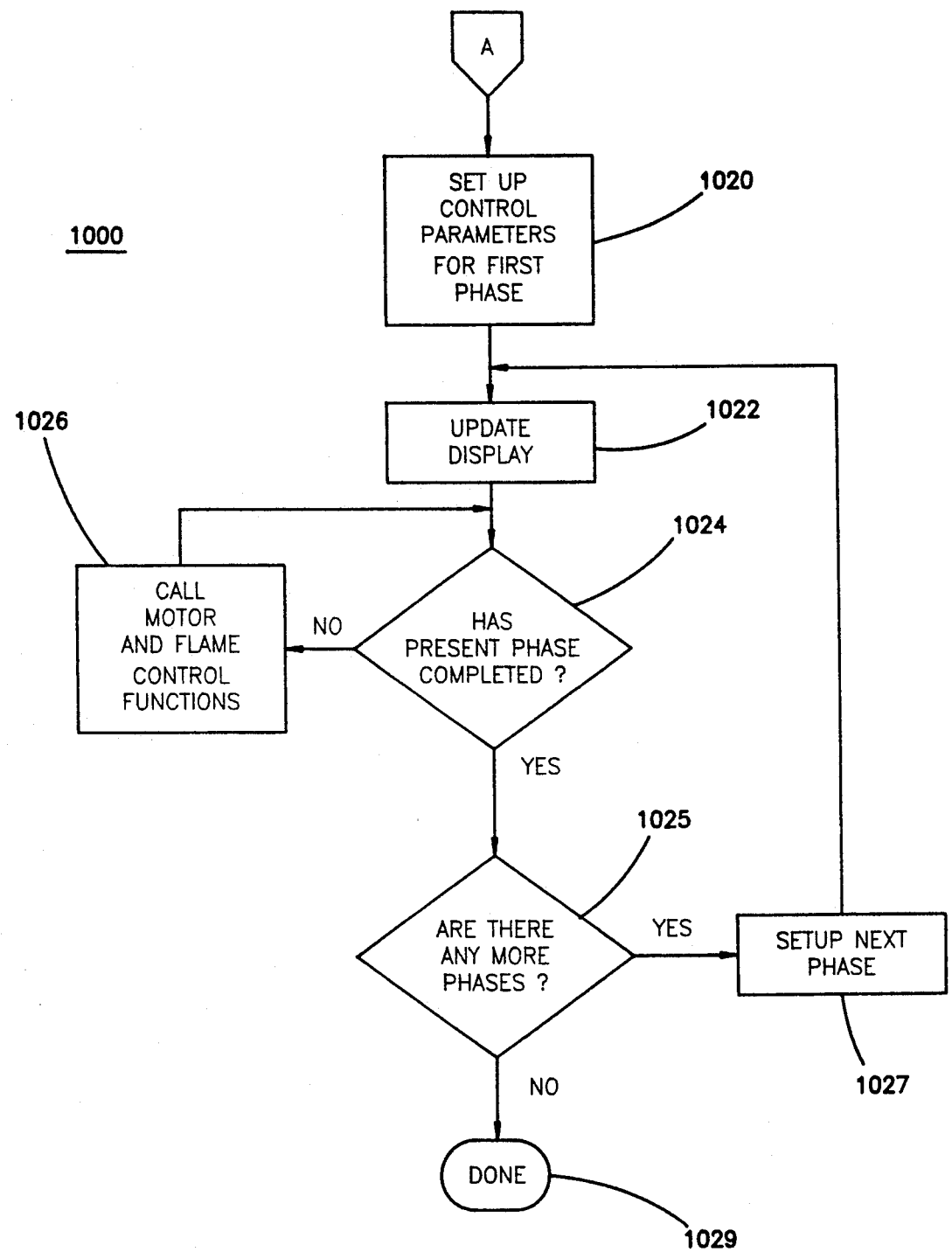
Figure 21C:
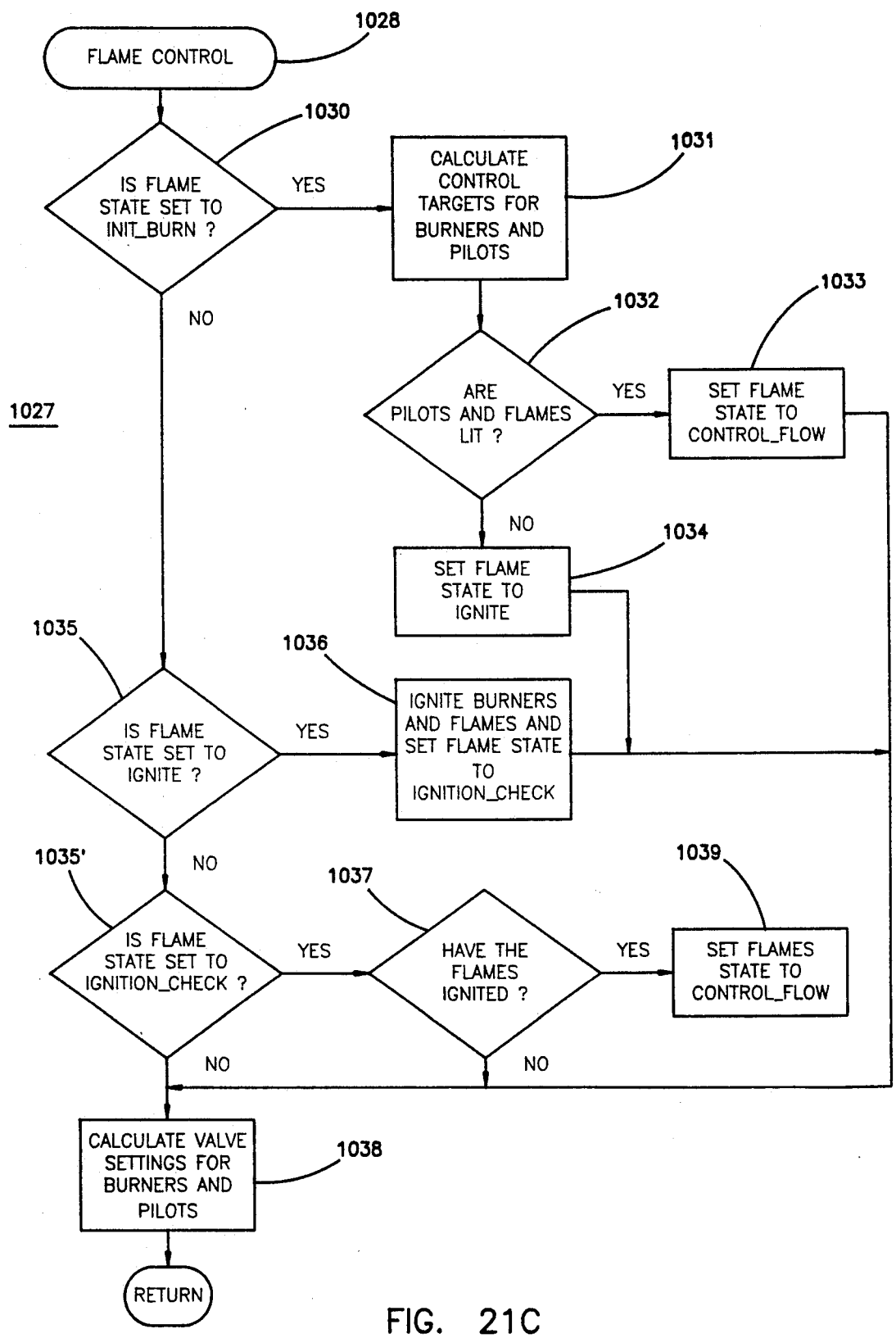

The program is contained by a diskette 905 (FIG. 19) such as a high-density 3-½ inch disk which can be programmed for a variety of selectable sample materials to be formed into a sample bead. Thus a single diskette may identify and include operational parameters for a number of different samples which can be operator selected and which will be agitated and heated to the necessary parameters according to the program entered into the diskette by the manufacturer of the equipment. Thus for example, when melting silicon dioxide, the flame temperature may be controlled at 1300° C., while the agitation pattern may be in the form of a W pattern by appropriate control of the X-Y motors and the time for the sample melt to be heated and agitated can be set for about 5 minutes with the fluxes and wetting agents noted earlier. The amplitude, frequency, and ratio of the X-Y axis motion for each type of sample is determined empirically and entered into the program. FIGS. 21A and 21B show the overall program flow diagram while FIGS. 21C–21J are flow diagrams for subroutines called from the main flowchart of 21A and 21B.

Beginning now with the description of the program 1000 and particularly the main program flow diagram, upon activation of the instrument, an execute command is entered by an appropriate operator push-button switch on keyboard 28 as indicated by block 1001. Actuation of the switch provides a display prompt to the operator to select a particular method to execute (i.e. a particular sample which will be of a standard selected weight together with a flux for that sample) as indicated by block 1002. This information is entered by the operator using keyboard 28. The number of samples and therefore the active number of burners is then queried by the program and this information entered as indicated by block 1004. The selected parameters are then read from the program diskette 905 (FIG. 19) by the floppy drive 904 and the program corresponding to the selected sample is written into the RAM memory of the CPU 901 for controlling the instrument. The transfer of the selected program information from the diskette is indicated by the flow diagram block 1006.

The program then tests, as indicated by block 1008, to determine whether there is a dispense phase for a nonwetting agent. As noted above, some samples, such as peroxide samples, remain liquid and are not transferred to a casting dish and therefore do not require nonwetting agents. Typically powdered samples will utilize a nonwetting agent and the program would normally proceed to block 1010 in which the assembly 600 is moved to a forward position extending the scoops 602, 604 and 606 for filling with a nonwetting agent. Once manually filled by the operator, the operator enters a confirmation command as indicated by block 1012 and the scoops are then retracted and a flag is set on the program to again extend and rotate the scoops at the appropriate time in the cycle of operation as indicated by block 1014. Naturally, if there is no dispensing phase of the cycle of operation, the test of block 1008 would be negative and the program would proceed directly to the test of block 1016 which tests to determine whether or not a casting phase is to be required.

The casting phase, as discussed above, pertains to the pouring of a sample melt into a casting dish requiring the selective operation of both the agitating mechanism in a pouring mode as well as the casting dish control assembly 400. If the selected method requires a casting phase, which is typical, the flag is set for execution of the casting subroutine shown in FIGS. 21H-21J at the appropriate time.

The main program then proceeds as indicated by interconnection block A in FIGS. 21A and 21B to call up the control parameters for the first phase of the sample preparation selected as indicated by block 1020. Each phase refers to a sequence of operations and flags set as time progresses during a complete cycle of operations. Thus the first action subsequent to the manual filling and retraction of the nonwetting agent scoop, would be to ignite the pilot burners after the operator has manually placed measured amounts of sample and flux material in the crucibles and lowered the crucibles into the crucible holders. The next action would be to actuate the pilot burner assembly to tilt the assembly 500 rearwardly to ignite the main burners. Thus, the sequence during each of these phases require various flags to be set to generate sequential control signals for controlling devices such as the motors, cylinders, and the solenoid valves and the like are set for the particular conditions selected by the program to sequentially run the instrument through a complete cycle of operation.

As each of the phases is initiated, the digital display 908 indicates the initiation of the phase to the operator as indicated by block 1022. The main program then tests, as indicated by block 1024, whether or not the selected first phase has been completed. If not, the first phase motor and flame control subroutines shown in FIGS. 21C and 21D respectively are called up to initiate a cycle of operation as indicated by block 1026.

The flame control subroutine controls the pilot burners as well as the solenoid and pressure valves for the main burners during a cycle of operation to successively apply heat to the crucibles and casting dishes in a temperature controlled manner in which the flame temperature and therefore the sample temperature is controlled by varying the air and gas supplied to the burners and pilots. The flame control subroutine 1027 (FIG. 21C) is initiated at block 1028 which occurs once the parameters have been loaded for the first phase of the cycle of operation. As indicated by block 1030, the program tests to determine whether or not the initiate burn flag is set. If it is, the program, as indicated by block 1031, calculates the various control targets for the servo valves providing compressed air and combustion gas to the burner for the selected sample and flame temperature corresponding to such sample.

As indicated by block 1032, the system detects through a sampling of signals from the sensor 544 of the pilot assembly, whether a pilot has been lighted. If it has, it is indicated by an affirmative response to test 1032, the valves are opened for the main burners as indicated by block 1033 to initiate ignition of the main burners with a preselected flame control. If the pilots are not lighted, a control signal is sent as indicated by block 1034 to cause their ignition. The program then loops through block 1026 again to block 1028 through the return path and the test of block 1030 is negative at which time the ignite main burner flag is detected as indicated by block 1035 causing the pilot burner control to tilt rearwardly for the ignition of the main burners as indicated by block 1036. This ignites the main burners at their predetermined flow rates of gas and compressed air to achieve the desired sample melting temperature during the agitation and fusion of the powdered sample and flux material. Once the burner ignite command is sent, as indicated by block 1036, the program cycles to the ignition check block 1035' to determine if the flag is set to check for ignition. If it is, the program sequences to block 1037 for checking ignition. Temperature feedback information from the thermocouples also are employed by the CPU to control the valves to achieve the desired temperature. If the flames are not lit as indicated by block 1037, the valve settings for the burners and pilots are calculated as indicated by block 1038 and the program cycles until the flame state flag is set to the control flow state as indicated by block 1039. Once the burners are ignited, the program cycles to block 1042 of FIG. 21D for controlling the agitation of the crucible as now described.

Figure 21D:
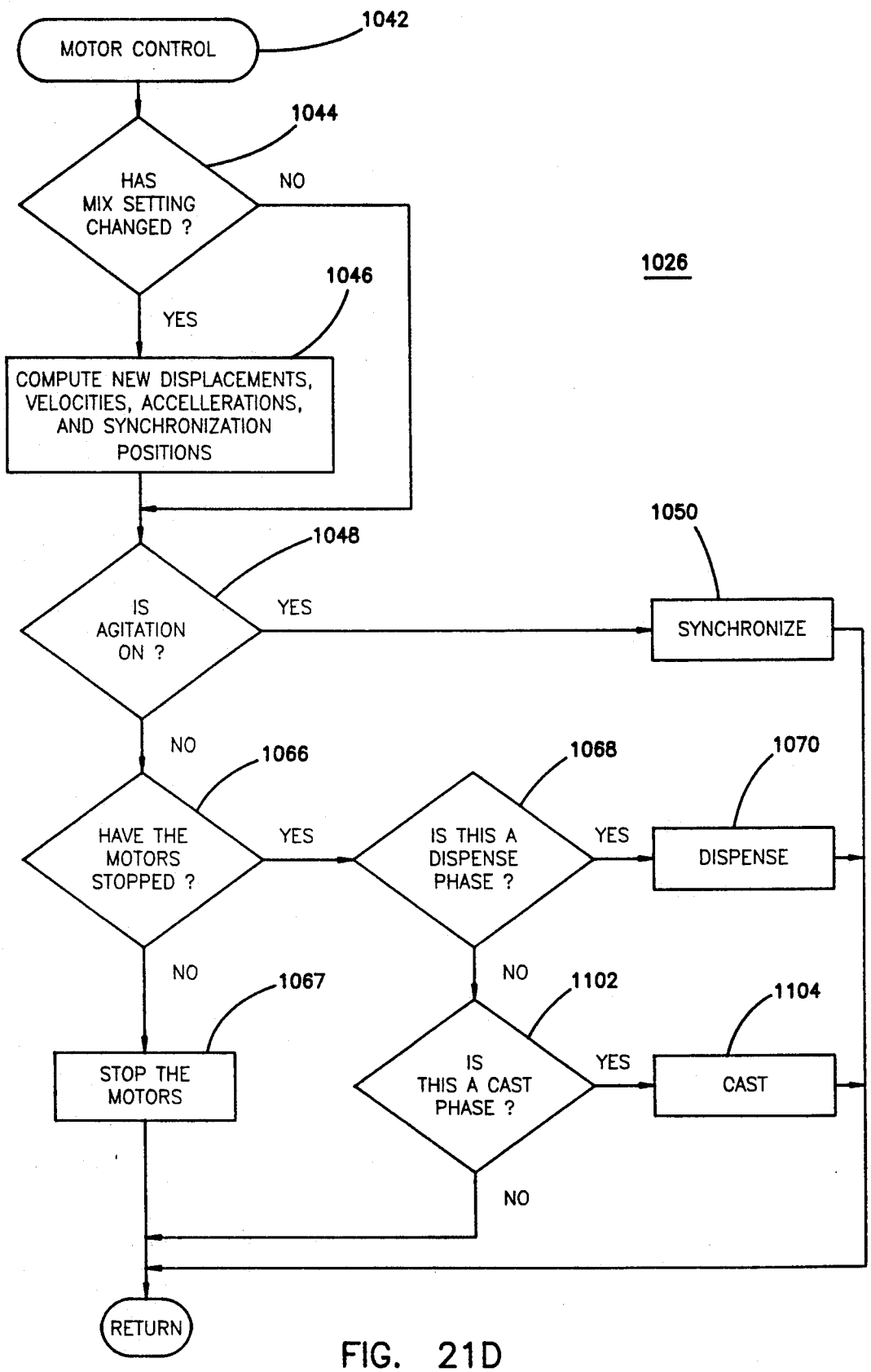
Figure 21E:
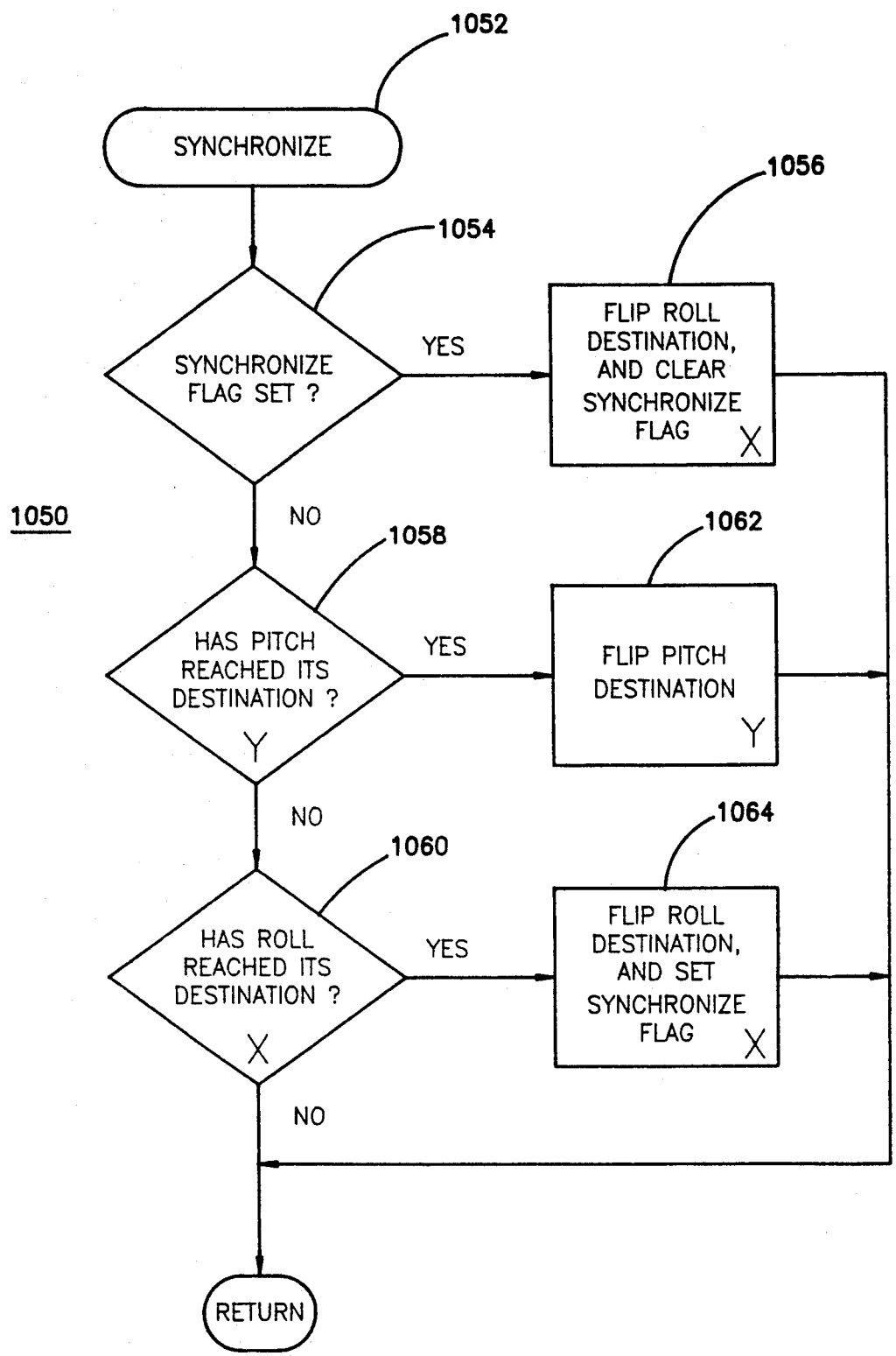

The motor control subroutine 1026 is shown in FIG. 21D beginning with block 1042 where the subroutine is started. The program tests, as indicated by block 1044, whether or not the agitation or mix setting has been changed from the programmed schedule. If it has not been, which is typical, the previous parameters to achieve a desired agitation sequence including the trajectory and synchronization parameters necessary to achieve that sequence are maintained. If however, the agitation setting has been changed from the previously selected sequence in RAM memory, the program recomputes the new parameters and enters them into the CPU as indicated by block 1046. The Program then tests to determine if agitation is under way and if it is, synchronization according to the desired pattern is achieved as indicated by block 1050 which is a separate subroutine shown in FIG. 21E.

The synchronization subroutine begins at block 1052 first to detect whether the synchronization flag is set as indicated by block 1054. If it is, the roll or X-axis destination flag is set to reverse the direction of motion of the crucible agitation motor 240 when feedback information from the optical encoder for the X-axis motor 240 has reached the end of desired travel for the program's agitation length or degree of rotation. The program then clears the synchronization flag and returns to block 1048 FIG. 21D) and tests to determine whether the agitation control is still taking place according to the time period set in block 1046. If it is, the program sequences again through test block 1054 which now will indicate a negative response and therefore the program tests the pitch destination to determine whether the Y-axis motion has reached its programmed travel limit as indicated by block 1058. If it has not, it tests to determine whether the roll or X-axis has reached its end of travel position as indicated by block 1060 and if not, the program test runs through test 1048 and continues to control the X-Y motors (240 and 230 respectively) in the same direction as indicated by blocks 1062 and 1064. If either the X or Y motors has reached the end of travel, the decision from blocks 1058 and 1060 will be affirmative and a reversal control signal will be sent to reverse the direction of the motor operation as indicated by blocks 1062 and 1064.

Once the time for the crucible agitation has expired, the test on block 1048 will be negative and the next step in the sequence is a test to determine whether the X-Y motors have stopped as indicated by block 1066 in FIG. 21B. If the motors have stopped, the program tests to determine if a dispense phase has been called for as indicated by block 1068 and if it has been, the dispensing subroutine as indicated by block 1070 is called up which is shown in FIGS. 21F and 21G.

The dispense subroutine 1070 begins with a dispense command as indicated by block 1072 and the program tests to determine if the flag is set to extend the dispensing spoons as determined by block 1074. The program extends the spoons and sets the dispense flags state to cause the dispensing of the nonwetting agent as indicated by block 1078. The program then recycles through block 1068 and when the block 1074 is tested, the program proceeds to the test block 1080. If the pour agent flag is previously set as it would have been by block 1078, an affirmative reply tells the program to test to determine whether the spoons are in an extended position over the crucibles. If they are not, the program recycles until the cylinders 640 and 642 have advanced the spoons whereupon the test from block 1082 is affirmative and the spoons are then inverted to dispense the nonwetting agent as indicated by block 1084 setting the flag to dispense delay.

Figure 21F:
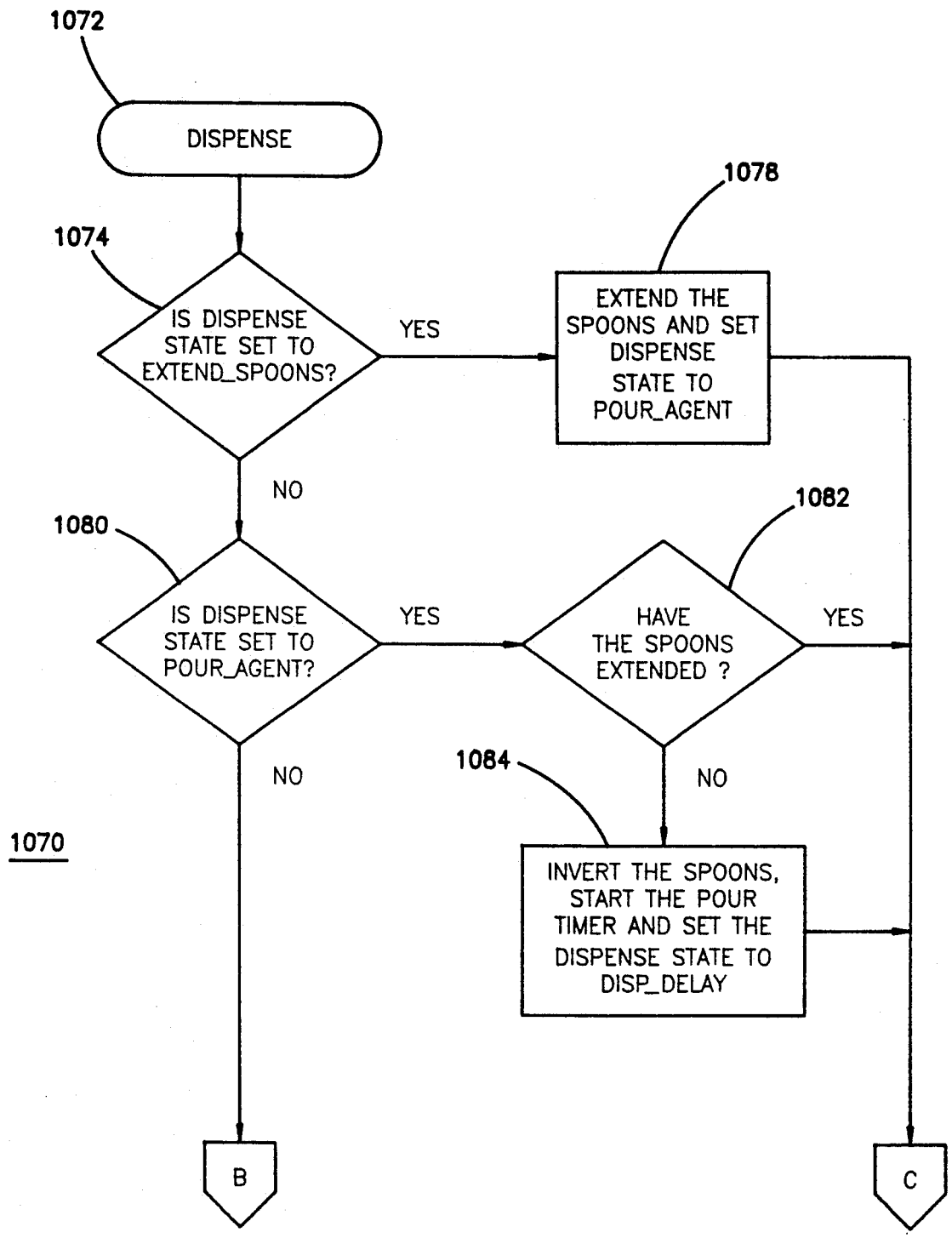
Figure 21G:
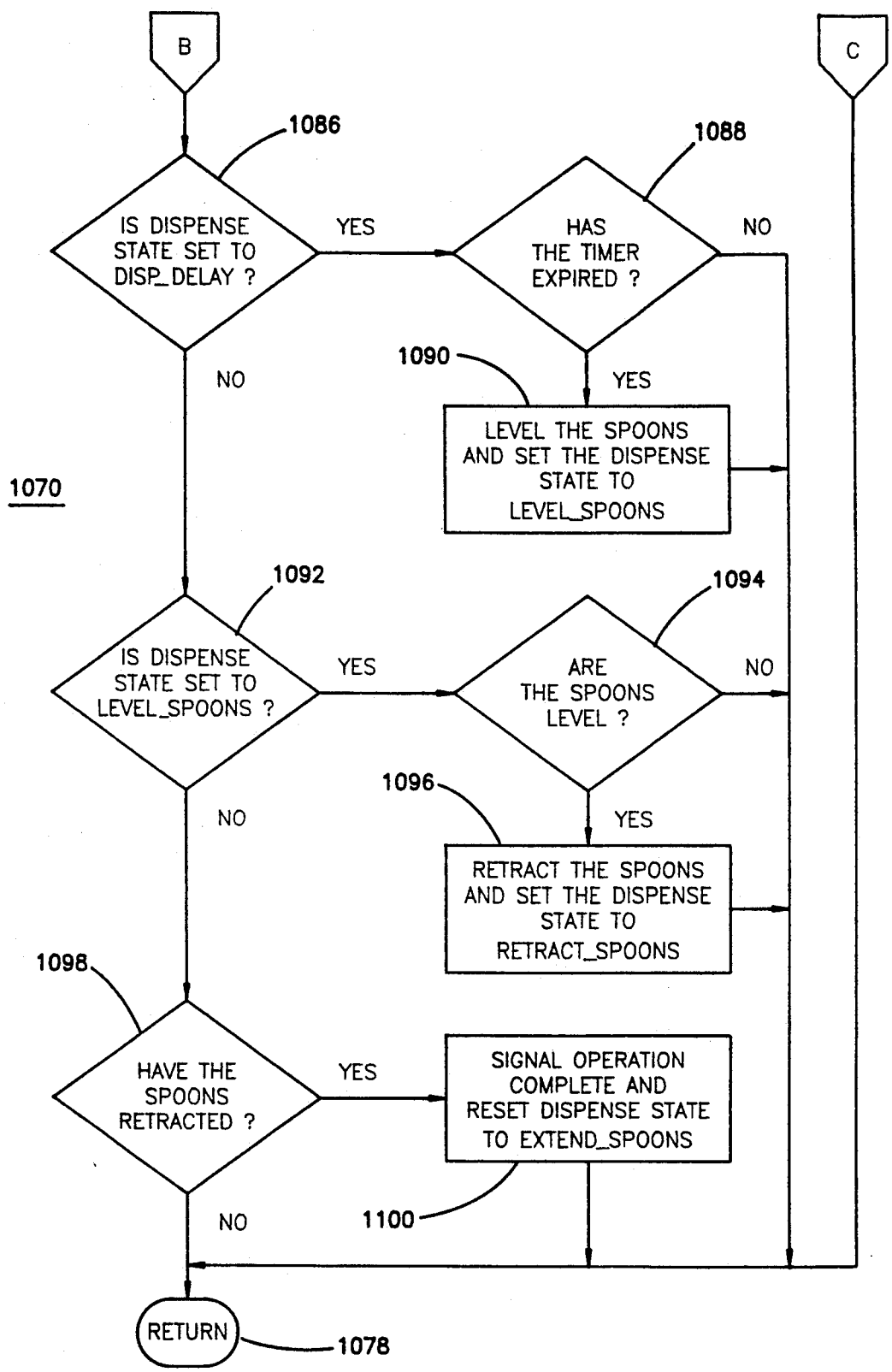

The program then recycles through a negative response in block 1080 to interconnecting inputs B of FIGS. 21F and 21G to determine if the dispense delay is set, which it will have been, through block 1084 as indicated by the test of block 1086. An affirmative reply checks to determine whether the delay timer has timed-out as indicated by block 1088 giving the holders 695 sufficient time to rotate the scoops for dumping the nonwetting agent into the open mouths of the crucibles. If the timer has not timed-out, the program recycles until the timer has timed-out at which time the spoons are returned to their neutral or level position as indicated by block 1090 setting a level spoon flag. The program then again recycles this time obtaining a negative reply in test 1086 and goes to block 1092 and tests to determine whether the level spoon flag is set. Since it has been, it detects the position of the rack driving the spoons through suitable sensor providing position signals to the CPU to indicate that the spoons are level as indicated by block 1094. If they are not, the program continues cycling with the motor 695 driving the rack until the spoons are level whereupon an affirmative response is detected at block 1094 and the program proceeds to retract these spoons and sets the flag indicating the spoons have been retracted as indicated by block 1096. The program recycles vertically downwardly through blooks 1086 and 1092 to test block 1098 which determines by a suitable sensor when the mechanism 600 has been retracted to a position rearwardly in the instrument cabinet away from the crucibles (i.e. in a position shown in FIG. 2). Once this has been achieved a signal is set indicating an affirmative reply to test 1098 and as indicated by block 1100, the dispensing operation has been completed and a flag is set to respond to the next extend spoon command in block 1074 during the next cycle of operation.

The program then again cycles through the motor control program subroutine 1026 once the dispensing subroutine has been completed and determines in block 1068 that the system is no longer in a dispensing phase but may have received a casting phase flag as indicated by block 1102 in FIG. 21D. If there is not a casting flag, the program returns to the main program input to block 1024. It is noted that if the agitation motors have not stopped as indicated by a negative test in block 1066, a stop motor command is generated as indicated by block 1067 to initiate the dispensing and casting operation. If a cast operation is called for as indicated by an affirmative test in block 1102, a casting routine 1104 is called up and is shown in detail in FIGS. 21H-21J now described.

Figure 21H:
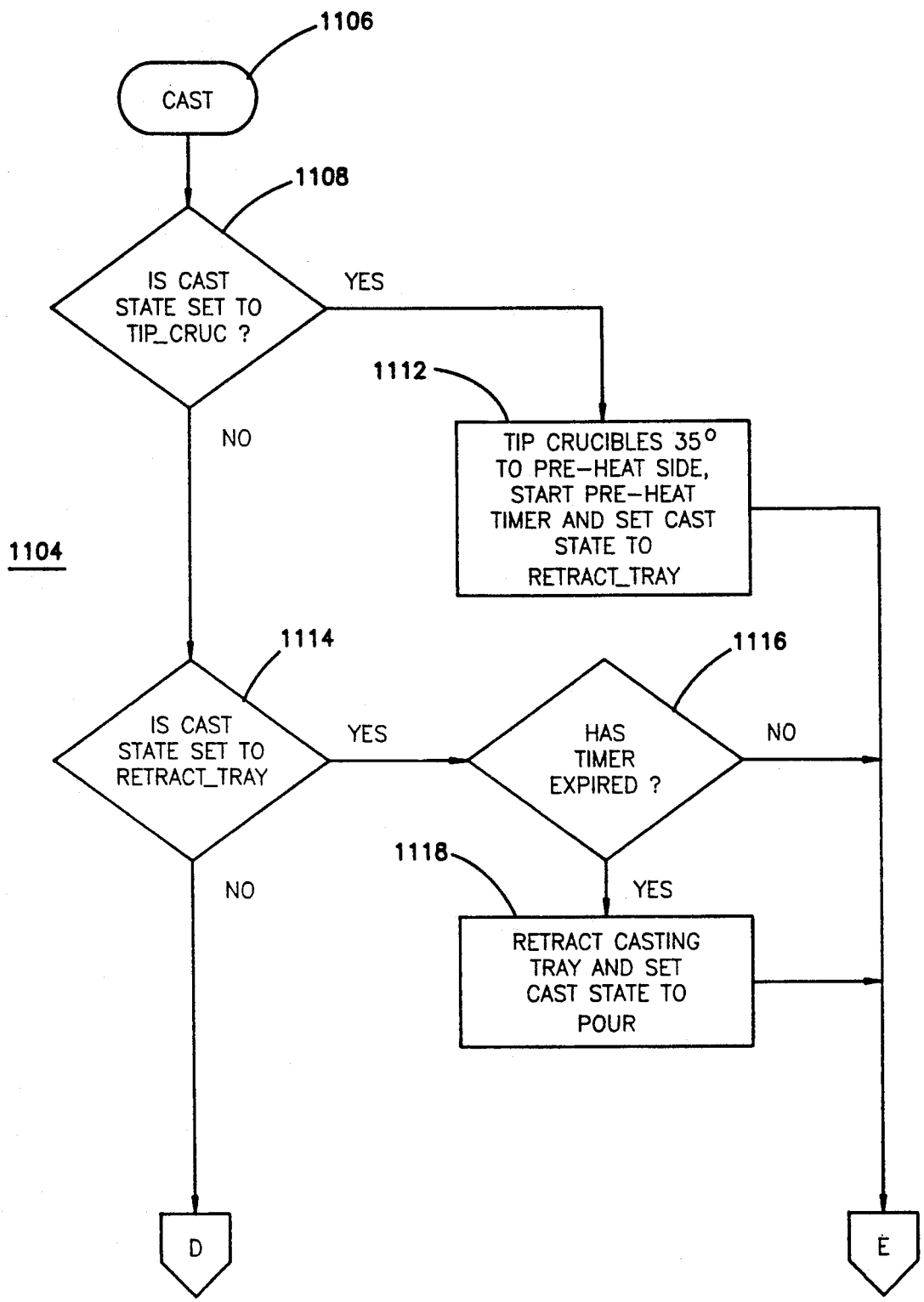
Figure 21I:
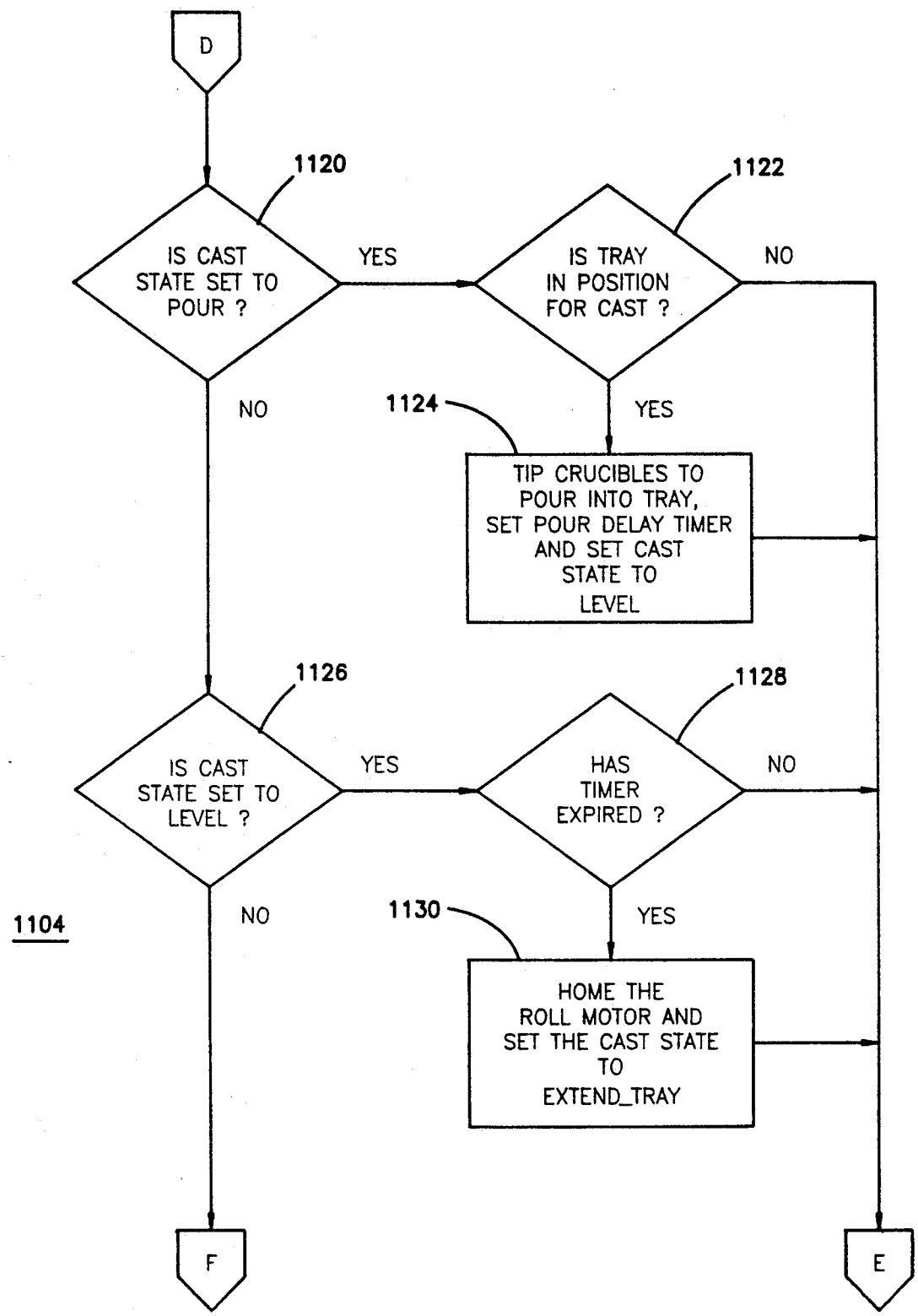
Figure 21J:
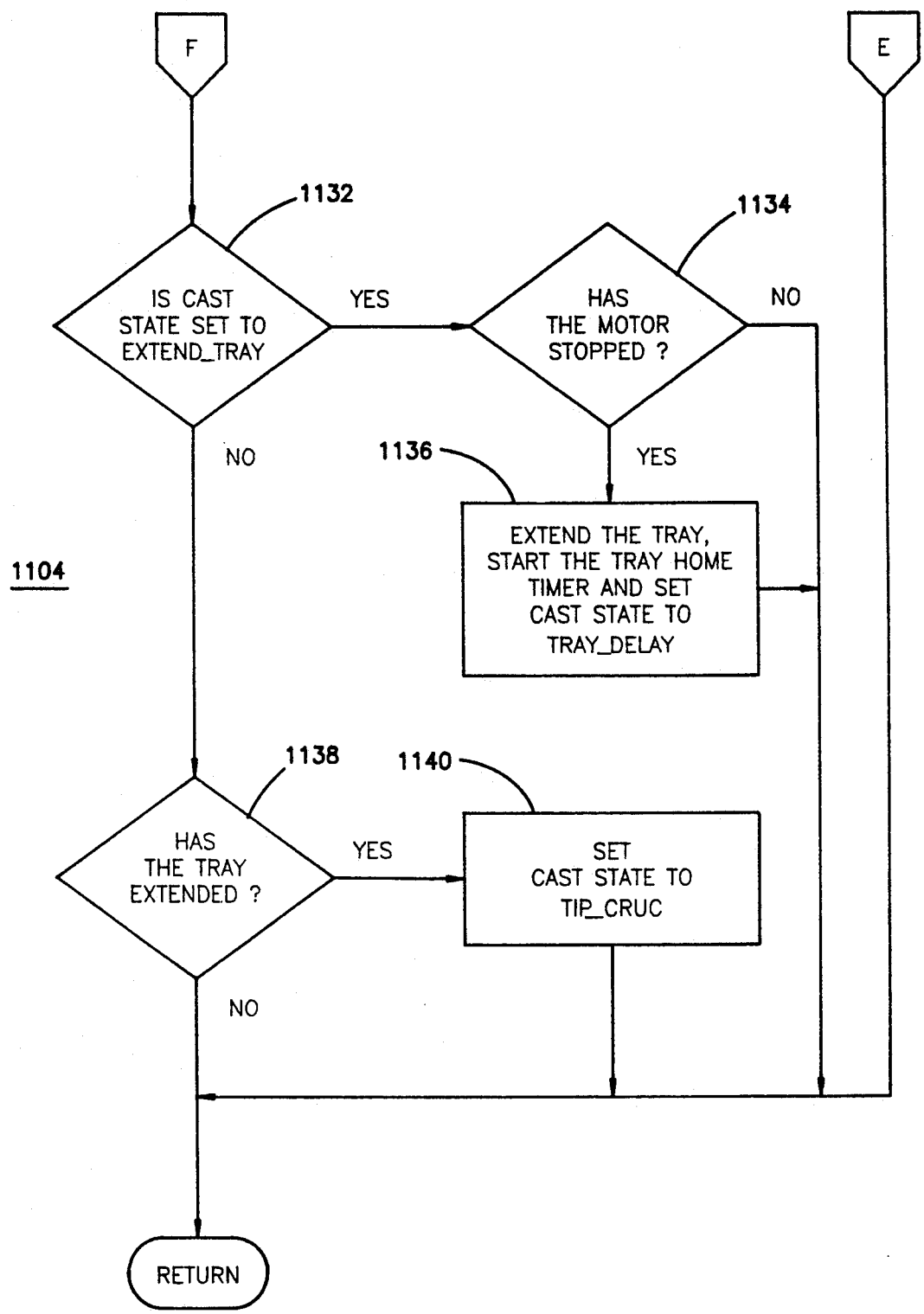

The casting subroutine shown in FIGS. 21H-21J controls the X-axis motor to provide pouring of the sample from a crucible into a casting dish after the crucible has been tilted 35° for preheating the side of the crucible. It also controls the operation of the casting dish control mechanism 400 to move in a position shown in FIG. 14 for receiving the sample melt. Upon receipt of the casting command as indicated by block 1106, a test is conducted to determine if a tipped crucible command flag has been set as indicated by block 1108. The crucibles are tipped approximately 35° to preheat the side area 134 of the crucible as described earlier for a predetermined period of time. A preheat timer is set for preheating the casting dishes as well as a retract tray flag for controlling the casting tray assembly 400 as indicated by block 1112. Once this operation has been completed the program returns to determine whether the retract tray flag is set as indicated by block 1114 and if so, whether the timer has expired as indicated by block 1116 for the preheating cycle. If it has not been, the pilot burners continue to preheat the casting dishes until the timer has expired which then generates a control signal through the CPU to actuate cylinder 440 to retract the casting tray from above the pilot burners to the casting position shown in FIG. 14.

The subroutine proceeds as indicated by FIG. 21I through interconnection D to determine if a pour flag has been set as indicated by block 1120. If it has been, a position sensor is sampled to determine whether the assembly 400 is in a retracted position ready for pouring as shown in FIG. 14 as indicated by block 1122. If it has not been, the program cycles until the cylinder 440 has had sufficient time to retract the guide rods 432 holding the table 410 with the casting dishes therein. Once the dishes are in position for casting, an affirmative decision on block 1122 causes the program to proceed to block 1124 which provides control signals to tip the crucible beyond the 35° heating stage to pour the sample melt into one or more of the casting dishes depending on how many of the crucible samples are being processed.

After a predetermined time sufficient for the pouring and casting step to be accomplished, a level flag is set for leveling the crucibles and the program proceeds to the beginning of the casting cycle at block 1106 proceeding downwardly through interconnect D to test block 1126 in FIG. 21I to determine whether the flag has been set and if it has been, has the timer expired for accomplishing the level position. If it has not, the program cycles until the timer has expired, in which case the X-axis control motor is operated until it reaches the home position for leveling the crucibles as indicated by block 1130 and a flag is set again to generate a control signal to extend the crucible casting dishes to their forwardmost position for operator access to the samples. The program then proceeds through interconnect F to test block 1132 to determine whether the extend tray flag has been set and if it has, has the leveling motor stopped as indicated by block 1134. If it has not, the program proceeds until the leveling motor has stopped and the extend cylinder 440 actuated as indicated by block 1136 to extend the tray 410 while setting a timer to provide a sufficient time for the tray to be extended.

The program then proceeds to detect a now negative test of block 1132 through the next cycle of the program and the CPU tests a sensor to determine at block 1138 to determine whether the apparatus 400 is in its extended position. If it is, the tip crucible flag is again set for the next cycle of operation as indicated by block 1140 and the program returns to the main program at block 1024 in FIG. 21B. The program then tests to determine if there are any more phases as indicated by block 1025 in FIG. 21B and if affirmative, the next phase is started as indicated in block 1027. Such phase may include for example, a cooling phase in which the program causes the CPU to control the valves to the pilot burners over which the casting dishes are positioned to turn on either the air and gas for a pilot flame, or the compressed air for a predetermined time period and at a predetermined pressure under control of the proportional servo valve to provide a controlled rate of cooling to the casting dishes for such predetermined period of time. When all of the phases of a cycle of operation have been completed as indicated by block 1029, a suitable signal is provided to the digital display 908 to display to the operator an indication of the completion of a cycle of operation. The instrument may be opened and the samples removed from the casting dish holding assembly 400 for subsequent analysis.

It will become apparent to those skilled in the art that various modifications to the preferred embodiments of the invention as described herein can be made without departing from the spirit or scope of the invention as defined by the appended claims.

The embodiments of the invention in which an exclusive property or privilege is claimed are defined as follows.

1. An apparatus for the preparation of an analytical sample comprising:
   crucible holding means for holding a crucible above a burner;
   a burner positioned below said crucible holding means for heating the contents of a crucible held therein; and
   agitation means coupled to said crucible holding means for agitating said crucible holding means along independently controlled separate axes for mixing together a sample material and flux material in a crucible held by said holding means as the crucible is heated by said burner.

2. The apparatus as defined in claim 1 wherein said agitation means comprises at least one first mounting member for supporting said crucible holding means, and first moving means for moving said at least one first mounting member about a first axis of rotation for the movement of said crucible holding means and a crucible positioned therein about said first axis.

3. The apparatus as defined in claim 2 wherein said agitation means further includes a second mounting member and second moving means coupled to said second mounting member for moving said second mounting member about a second axis different than said first axis, and wherein said first mounting member and said first moving means are mounted to said second mounting member.

4. The apparatus as defined in claim 3 wherein said first and second axes are generally orthogonally related to one another.

5. The apparatus as defined in claim 4 wherein said mounting member comprises clamp means for removably supporting said crucible holding means.

6. The apparatus as defined in claim 5 wherein said first moving means includes a rotatable shaft coupled to said clamp means and gear means coupled to said rotatable shaft.

7. The apparatus as defined in claim 6 wherein said first moving means further includes a rack supported by said second mounting member and engaging said gear means for the rotation of said crucible holding means in response to the movement of said rack.

8. The apparatus as defined in claim 7 wherein said first moving means further includes a motor for driving said rack.

9. The apparatus as defined in claim 8 wherein said second mounting member includes an elongated member for receiving a plurality of said clamp means, and said second moving means includes pivot arm means for moving said elongated member in an arc about said second axis.

10. The apparatus as defined in claim 9 wherein said crucible holding means includes a first generally planar member having an extension at one end for coupling said planar member to said clamp means.

11. The apparatus as defined in claim 10 wherein said planar member of said crucible holding means includes an aperture for receiving a crucible, said planar member further including an open slot adjacent said aperture extending through an edge of said planar member for providing direct access to a side portion of the crucible.

12. The apparatus as defined in claim 11 wherein said crucible holding means further includes a locking arm mounted to said planar member and movable between a first position allowing insertion and removal of a crucible and a second position holding a crucible in place on said planar member for different positions of said planar member.

13. An instrument for the preparation of an analytical sample comprising:
   means for holding a crucible for agitation of the contents therein;
   burner means positioned below said crucible holding means for the heating of sample material contained by a crucible;
   means for moving said crucible holding means to agitate and thereby mix the contents of a crucible during the heating of the crucible;
   electrically controlled elements operatively connected to said means for moving said crucible holding means for controlling the agitation pattern of said holding means along independent separate axes and to said burner means for controlling said burner means; and
   an electrical circuit including a microprocessor and program means for said microprocessor to control a cycle of agitation and heating of sample material contained in a crucible in a predetermined manner.

14. The apparatus as defined in claim 13 wherein said program means comprises a computer program stored on a floppy disk and wherein said electrical control system further includes a disk drive for transferring said program from said disk to said microprocessor.

15. An instrument for the preparation of an analytical sample comprising:

means for holding a crucible for agitation of the contents therein;

means for moving said crucible holding means along independent separate axes to agitate and mix the contents of a crucible held by said crucible holding means; and an electrical control circuit operatively coupled to said crucible holding means and including a microprocessor and program means for said microprocessor to control a cycle of agitation in a predetermined manner, wherein said program means comprises a computer program stored on a floppy disk and wherein said electrical control system further includes a disk drive for transferring said program from said disk to said microprocessor.

* * * * *

UNITED STATES PATENT AND TRADEMARK OFFICE
CERTIFICATE OF CORRECTION

PATENT NO.   : 5,269,827
DATED        : December 14, 1993
INVENTOR(S)  : Lenke, et. al.

It is certified that error appears in the above-indentified patent and that said Letters Patent is hereby corrected as shown below:

```
Column  2, line 63, "oooling" should be --cooling--;
Column  6, line 51, "drum 26" should be --drum 261--;
Column  8, line 65, "oircuit" should be --circuit--;
Column 11, line 66, "oircuit" should be --circuit--;
Column 12, line 30, "imput port 30" should be --imput port--;
Column 12, line 55, "oircuit" should be --circuit--;
Column 14, line 58, "oontrolling" should be --controlling--;
Column 17, line 44, "reoycles" should be --recycles--;
Column 20, claim 5, line 8, before "mounting" insert --first--;
Column 20, claim 13, line 63, after "electrical" insert --control--;
```

Signed and Sealed this

Twentieth Day of September, 1994

Attest:

BRUCE LEHMAN

Attesting Officer

Commissioner of Patents and Trademarks